(12) United States Patent
Xi et al.

(10) Patent No.: US 9,567,364 B2
(45) Date of Patent: Feb. 14, 2017

(54) NUCLEOTIDE AND/OR OLIGONUCLEOTIDE AND PREPARATION PROCESS THEREOF

(75) Inventors: Zhen Xi, Tianjin (CN); Zicai Liang, Beijing (CN); Jinyu Huang, Tianjin (CN)

(73) Assignee: Suzhou Ribo Life Sciene Co., Ltd., Kunshan (CN)

( * ) Notice: Subject to any disclaimer, the term of this patent is extended or adjusted under 35 U.S.C. 154(b) by 124 days.

(21) Appl. No.: 13/811,295

(22) PCT Filed: Jul. 20, 2011

(86) PCT No.: PCT/CN2011/077353
§ 371 (c)(1),
(2), (4) Date: Jan. 21, 2013

(87) PCT Pub. No.: WO2012/013127
PCT Pub. Date: Feb. 2, 2012

(65) Prior Publication Data
US 2013/0123482 A1   May 16, 2013

(30) Foreign Application Priority Data

Jul. 27, 2010   (CN) .......................... 2010 1 0240545

(51) Int. Cl.
| | |
|---|---|
| C07H 21/02 | (2006.01) |
| C07H 21/04 | (2006.01) |
| C07H 21/00 | (2006.01) |
| C07H 19/04 | (2006.01) |
| C07H 19/20 | (2006.01) |
| C07H 19/10 | (2006.01) |
| C07H 19/048 | (2006.01) |
| C07H 19/167 | (2006.01) |

(52) U.S. Cl.
CPC .............. *C07H 21/02* (2013.01); *C07H 19/10* (2013.01); *C07H 19/167* (2013.01); *C07H 19/20* (2013.01); *C07H 21/04* (2013.01); *Y02P 20/55* (2015.11)

(58) Field of Classification Search
CPC ....... C07H 19/10; C07H 19/167; C07H 19/20; C07H 21/02; C07H 21/04
See application file for complete search history.

(56) References Cited

U.S. PATENT DOCUMENTS

| 5,003,097 | A | 3/1991 | Beaucage et al. |
| 5,639,867 | A | 6/1997 | Brill |
| 8,569,476 | B2 * | 10/2013 | Xi et al. .................. 536/25.3 |
| 2007/0249548 | A1 | 10/2007 | Kitade et al. |
| 2011/0237786 | A1 | 9/2011 | Xi et al. |

FOREIGN PATENT DOCUMENTS

| CN | 1111249 A | 11/1995 |
| WO | 9204358 A1 | 3/1992 |
| WO | 94/15946 | 7/1994 |
| WO | 9640708 A2 | 12/1996 |
| WO | 2006/030906 A1 | 3/2006 |
| WO | 2006/095739 A1 | 9/2006 |
| WO | 2010/037326 A1 | 4/2010 |

OTHER PUBLICATIONS

Flockerzi et al., "266. Nucleotide, XXI. Synthese und Eigenschaften Dihydrouridin-haltinger Oligonucleotide," Helvetica Chimica Acta, 66(8), 2641-3651 (1983).*
Sung, W. I., Synthesis of 4-(1,2,4-Triazol-1-yl)pyrimidine-2(1H)-one Ribonucleotide and Its Application in Synthesis of Oligoribonucleotides, Journal of Organic Chemistry, 47(19), 3623-3628 (1982).*
Ogilvie et al., "The Chemical Synthesis of Oligoribonucleotides VII. A Comparison of Condensing Agents in the Coupling of Silylated Ribonucleosides," Nucleic Acids Research, 8(9), 2105-2116 (1980).*
International Search Report for corresponding International Application No. PCT/CN2011/077353 mailed Oct. 27, 2011 and English translation thereof.
Antkowiak et al., "Efficient Synthesis of Oligoribonucleotides" Bulletin De L'Academie Polonaise Des Sciences (1980) vol. 28, No. 7-8, pp. 537-541.
Bartel, "MicroRNAs: Genomics, Biogenesis, Mechanism, and Function" Cell (2004) vol. 116, pp. 281-297.

(Continued)

*Primary Examiner* — Lawrence E Crane
(74) *Attorney, Agent, or Firm* — Calfee, Halter & Griswold LLP

(57) ABSTRACT

Nucleotide and/or oligonucleotide represented by formula (1) and the liquid phase synthesis process thereof. The present invention provides a liquid phase synthesis process for preparing a nucleotide and/or an oligonucleotide, comprising a process for combining the nucleotide and/or oligonucleotide protective groups, in which, under the condition that the 2'-hydroxyl group is protected by a group with a sterically hindered silane structure, the 3' phosphate group(s) of the nucleotide and/or oligonucleotide is/are directly protected by (a)β-cyanoethyl group(s), and after the β-cyanoethyl group(s) is/are removed, the resulting product can directly participate in the next cycle of synthesis, wherein the synthesis reaction is carried out in a reaction flask or reaction kettle, without being limited by a solid carrier or synthesizer, so that the large scale preparation of oligonucleotides can be achieved.

Formula (1)

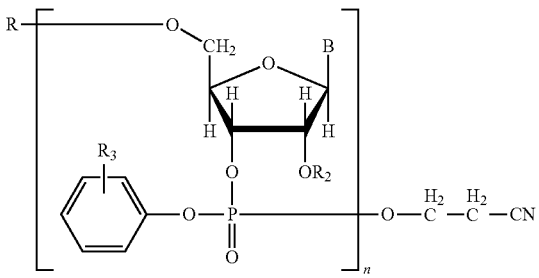

19 Claims, 3 Drawing Sheets

(56) References Cited

OTHER PUBLICATIONS

Charubala et al., "Synthesis and Properties of Adenylate Trimers A2'p5'A2'p5'A, A2'p5'A3'p5'A and A3'p5'A2'p5'A" Tetrahedron Letters (1980) vol. 21, pp. 1933-1936.
Charubala et al., "Nucleotides, XVIII.—Synthesis and Properties of Adenylyl-adenylyl-adenosines" Liebigs Ann. Chem. (1981) vol. 1981, Issue 12, pp. 2392-2406.
Flockerzi et al., "Nucleotides, XVII. Synthesis of Homogeneous Adenosyl-3',5'-oligomers by the Phosphotriester Method" Helvetica Chimica Acta (1983a) vol. 66, pp. 2018-2033.
Flockerzi et al., "Nucleotides, XVIII. Synthesis and Properties of (tert-Butyldimethylsilyl)guanosines, Guanosine-3'-Phosphotriesters and Guanosine-containing Oligonucleotides" Helvetica Chimica Acta (1983a) vol. 66, pp. 2069-2085.
Green et al., Molecular Cloning: A Laboratory Manual. Fourth Edition. (2012) Cold Spring Harbor Press, Cold Spring Harbor, New York. Table of Contents. 34 pages.
Hsu et al., "Synthesis Ano Physical Characterization of Bis 3'+ 5' Cyclic Dinucleotides (-NpNp-): RNA Polymerase Inhibitors" Nucleosides & Nucleotides (1985) vol. 4, No. 3, pp. 377-389.
Jones et al., "Synthesis of the 3'-Terminal Decaribonucleoside Nonaphosphate of Yeast Alanine Transfer Ribonucleic Acid" Tetrahedron (1980) vol. 36, pp. 3075-3085.
Kikuchi et al., "Evaluation of the 2NH2A-T Pair in Hybridization, I Synthesis of the DNA/RNA Hybrid Oligomers Containing 2-Aminoadenosines" Z. Naturforsch (1988) vol. 43b, pp. 623-630.
Napoli et al., "Facile Preparation of Cyclic Oligoribonucleotides" J. Chem. Soc. Perkin. Trans. (1993) Issue 7, pp. 747-749.
Reese, "Oligo- and poly-nucleotides: 50 years of chemical synthesis" Org. Biomol. Chem. (2005) vol. 3, pp. 3851-3868.
Roth et al., "Purification and Characterization of Murine Retroviral Reverse Transcriptase Expressed in *Escherichia coli*" J. Biol. Chem. (1985) vol. 260, No. 16, pp. 9326-9335.
Sambrook et al., Molecular Cloning: A Laboratory Manual. Third Edition. (2001) Cold Spring Harbor Press, Cold Spring Harbor, New York. Table of Contents. 21 pages.
Silber et al., "Nucleotides. XV. Synthesis and Properties of 2'-O-t-Butyldimethylsilyl-5'-O-monomethoxytritylribonucleoside-3'-phosphotriesters, Starting Materials for Oligonucleotide Syntheses" Helvetica Chimica Acta (1981) vol. 64, pp. 1704-1716.
Sung et al., "Modified phosphotriester method for chemical synthesis of ribooligonucleotides. Part I. Synthesis of riboundecaadenylate and two fragments constituting the sequence of R-17 translation control signal" Can. J. Chem. (1982) vol. 60, pp. 111-120.
Wu et al., "RNA Interference inhibits replication and expression of hepatitis B virus in mice" Natl. Med. J. China (Mar. 9, 2005) vol. 85, No. 9, pp. 630-634.
Ogilvie et al., "The chemical synthesis of oligoribonucleotides. 1X.I A comparison of protecting groups in the dichloridite procedure" (1980) Can. J. Chem., vol. 58, pp. 2686-2693.

\* cited by examiner

SEQUENCE LISTING

<160> NUMBER OF SEQ ID NOS: 18

<210> SEQ ID NO 1
<211> LENGTH: 21
<212> TYPE: RNA
<213> ORGANISM: Artificial Sequence
<220> FEATURE:
<223> OTHER INFORMATION: The sequence is synthesized

<400> SEQUENCE: 1
ccuugaggca uacuucaaau u                                              21

<210> SEQ ID NO 2
<211> LENGTH: 21
<212> TYPE: RNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (1)..(1)
<223> OTHER INFORMATION: protected by DMTr
<220> FEATURE:
<221> NAME/KEY: misc_feature
<222> LOCATION: (21)..(21)
<223> OTHER INFORMATION: protected by OE

<400> SEQUENCE: 2
ccuugaggca uacuucaaau u                                              21

<210> SEQ ID NO 3
<211> LENGTH: 11
<212> TYPE: RNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (1)..(1)
<223> OTHER INFORMATION: protected by DMTr
<220> FEATURE:
<221> NAME/KEY: misc_feature
<222> LOCATION: (11)..(11)
<223> OTHER INFORMATION: protected by PO

<400> SEQUENCE: 3
ccuugaggca u                                                         11

<210> SEQ ID NO 4
<211> LENGTH: 10
<212> TYPE: RNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (1)..(1)
<223> OTHER INFORMATION: protected by HO
<220> FEATURE:
<221> NAME/KEY: misc_feature
<222> LOCATION: (10)..(10)
<223> OTHER INFORMATION: protected by OE

<400> SEQUENCE: 4
acuucaaauu                                                           10

<210> SEQ ID NO 5
<211> LENGTH: 21
<212> TYPE: RNA
<213> ORGANISM: Artificial Sequence

```
<220> FEATURE:
<223> OTHER INFORMATION: The sequence is synthesized

<400> SEQUENCE: 5
uuugaaguau gccucaaggu u                                              21

<210> SEQ ID NO 6
<211> LENGTH: 11
<212> TYPE: RNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (1)..(1)
<223> OTHER INFORMATION: protected by DMTr
<220> FEATURE:
<221> NAME/KEY: misc_feature
<222> LOCATION: (11)..(11)
<223> OTHER INFORMATION: protected by PO

<400> SEQUENCE: 6
uuugaaguau g                                                         11

<210> SEQ ID NO 7
<211> LENGTH: 21
<212> TYPE: RNA
<213> ORGANISM: Artificial Sequence
<220> FEATURE:
<223> OTHER INFORMATION: Artificial sequence
<220> FEATURE:
<221> NAME/KEY: misc_feature
<222> LOCATION: (1)..(1)
<223> OTHER INFORMATION: protected by DMTr
<220> FEATURE:
<221> NAME/KEY: misc_feature
<222> LOCATION: (21)..(21)
<223> OTHER INFORMATION: protected by OE

<400> SEQUENCE: 7
uuugaaguau gccucaaggu u                                              21

<210> SEQ ID NO 8
<211> LENGTH: 19
<212> TYPE: RNA
<213> ORGANISM: Artificial Sequence
<220> FEATURE:
<223> OTHER INFORMATION: synthetic sequence

<400> SEQUENCE: 8
ccuugaggca uacuucaaa                                                 19

<210> SEQ ID NO 9
<211> LENGTH: 19
<212> TYPE: RNA
<213> ORGANISM: Artificial Sequence
<220> FEATURE:
<223> OTHER INFORMATION: synthetic sequence

<400> SEQUENCE: 9
ucaccauacu gcacucagg                                                 19

<210> SEQ ID NO 10
<211> LENGTH: 20
<212> TYPE: DNA
<213> ORGANISM: Artificial Sequence
<220> FEATURE:
<223> OTHER INFORMATION: upstream primer
```

```
<400> SEQUENCE: 10
actctctcgt cccttctcc                                                    20

<210> SEQ ID NO 11
<211> LENGTH: 20
<212> TYPE: DNA
<213> ORGANISM: Artificial Sequence
<220> FEATURE:
<223> OTHER INFORMATION: downstream primer

<400> SEQUENCE: 11
ggtcgttgac attgcagaga                                                   20

<210> SEQ ID NO 12
<211> LENGTH: 20
<212> TYPE: DNA
<213> ORGANISM: Artificial Sequence
<220> FEATURE:
<223> OTHER INFORMATION: upstream primer

<400> SEQUENCE: 12
ctctgctcct cctgttcgac                                                   20

<210> SEQ ID NO 13
<211> LENGTH: 20
<212> TYPE: DNA
<213> ORGANISM: Artificial Sequence
<220> FEATURE:
<223> OTHER INFORMATION: downstream primer

<400> SEQUENCE: 13
acgaccaaat ccgttgactc                                                   20

<210> SEQ ID NO 14
<211> LENGTH: 42
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: protected by DMTr
<220> FEATURE:
<221> NAME/KEY: misc_feature
<222> LOCATION: (42)..(42)
<223> OTHER INFORMATION: protected by OE

<400> SEQUENCE: 14
ccuugaggca uacuucaaau uuugaaguau ugccucaagg uu                          42

<210> SEQ ID NO 15
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: protected by DMTr
<220> FEATURE:
```

```
<221> NAME/KEY: misc_feature
<222> LOCATION: (21)..(21)
<223> OTHER INFORMATION: protected by PO

<400> SEQUENCE: 15
ccuugaggca uacuucaaau u                                               21

<210> SEQ ID NO 16
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: protected by DMTr
<220> FEATURE:
<221> NAME/KEY: misc_feature
<222> LOCATION: (21)..(21)
<223> OTHER INFORMATION: protected by OE

<400> SEQUENCE: 16
ccuugaggca uacuucaaau u                                               21

<210> SEQ ID NO 17
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: protected by HO
<220> FEATURE:
<221> NAME/KEY: misc_feature
<222> LOCATION: (21)..(21)
<223> OTHER INFORMATION: protected by OE

<400> SEQUENCE: 17
uuugaaguau gccucaaggu u                                               21

<210> SEQ ID NO 18
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: protected by DMTr
<220> FEATURE:
<221> NAME/KEY: misc_feature
<222> LOCATION: (21)..(21)
<223> OTHER INFORMATION: protected by OE

<400> SEQUENCE: 18
uuugaaguau gccucaaggu u                                               21
```

NUCLEOTIDE AND/OR OLIGONUCLEOTIDE AND PREPARATION PROCESS THEREOF

This application is a national phase of International Application No. PCT/CN2011/077353 filed Jul. 20, 2011, which claims priority to Chinese Patent Application No. 201010240545.1, filed Jul. 27, 2010.

FIELD OF THE INVENTION

The present invention relates to a nucleotide and/or oligonucleotide and its preparation process.

BACKGROUND OF THE INVENTION

The chemical synthesis of oligonucleotide refers to the process of connecting nucleotide units into an oligonucleotide chain by prompting the formation of 5'-3' phosphate diester bonds between nucleotide monomers. It relates to the synthesis of protected nucleotides.

At present, the common synthesis process of oligonucleotide is solid-phase synthesis process: firstly, the 5'-OH on nucleotide is protected by 4,4'-dimethoxytrityl (DMT), the amino on the base is protected by benzoyl, and the 3'-OH is activated by amino phosphite compound. The 3'-OH on the first nucleotide is combined with solid-phase resin, the protective group on 5'-OH is removed, a phosphite triester is formed between the exposed 5'-OH and the 3'-OH of the second nucleotide, which is activated by amino phosphite compound, the phosphite triester forms phosphotriester through iodination, and then trichloroacetic acid is added to remove the protective group on the 5'-OH of the second nucleotide. By now, the oligonucleotide chain is extended by one nucleotide unit, and may be put into the next round of extension reaction. After the synthesis of the whole oligonucleotide segment is completed through several rounds of extension reaction, concentrated ammonium hydroxide is used to remove the oligonucleotide segment from the solid-phase resin, and after deprotection and purification, oligonucleotide is obtained.

The advantages of the said solid-phase synthesis process lie in: 1) automation: all the synthetic reactions are automatically completed by a synthesizer; 2) short synthetic cycle; 3) high yield: the yield of single-step condensation reaction is greater than 98% in general. However, the solid-phase synthesis process also has some defects: 1) small synthetic scale: the scale of solid-phase synthesis does not exceed 100 μmol in general, which is far from meeting the requirement of the use in pharmaceutical raw materials; 2) difficulty in achieving high purity: due to the limitation of the synthesis process, it is inevitable that the obtained oligonucleotide contains non-target oligonucleotide segments with N−1, N−2 of base number, which are rather detrimental to pharmaceutical application; 3) serious waste: to realize sufficient reaction, in each synthetic cycle, often phosphoramidite monomers that are several times as much as the amount actually consumed by the reaction need to be added to realize excess, and after the cycle, a large amount of organic solvent has to be used as a washing solvent to wash away the unreacted phosphoramidite monomers; 4) high cost: the solid-phase carrier and phosphoramidite monomers needed by the reaction are expensive, resulting in high cost of oligonucleotide synthesis.

Due to the important function of oligonucleotide in life activities and the fast development of nucleic acid research technology, particularly the development of RNA interference technology and its potential clinical application value, large-scale synthesis of oligonucleotide is a matter of significance.

SUMMARY OF THE INVENTION

The object of the present invention is to overcome the defects of the current synthetic process of oligonucleotide, such as: small scale and high cost, and provide a process for large-scale synthesis of oligonucleotide.

The present invention provides a nucleotide and/or oligonucleotide as represented by Formula (1):

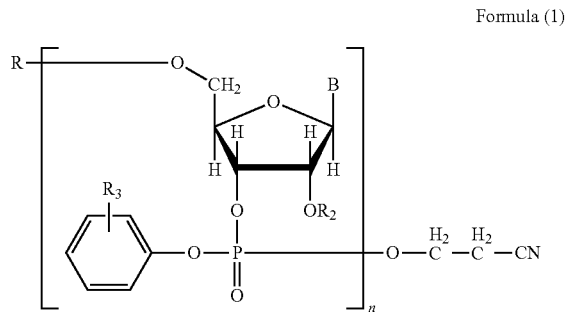

Formula (1)

wherein, R is H or $R_1$, and $R_1$ represents trityl, monomethoxytrityl, 4,4'-dimethoxytrityl or trimethoxytrityl;

n is an integer in the range of 1-100;

B represents guanine group with exocyclic amino group protected by acyl, adenine group with exocyclic amino group protected by acyl, cytosine group with exocyclic amino group protected by acyl, thymine group or uracil group, and B of each repeat unit is identical or different;

$R_2$ represents a group with a sterically hindered silane structure;

$R_3$ represents halogen atom, nitro or methoxyl.

Wherein, the group with a sterically hindered silane structure may be tert-butyl dimethyl silyl, phenyl dimethyl silyl, tert-butyl diphenyl silyl or triisopropyl silyl.

Wherein, the acyl may be benzoyl, isobutyryl or acetyl; halogen atom may be Cl or Br.

In the compound of Formula (1) provided by the present invention, when R is H, Formula (1) is equivalent to the following Formula (2) with x equal to or greater than 1; and when R is $R_1$, Formula (1) is equivalent to the following Formula (4).

The present invention further provides a process for liquid-phase synthesis of nucleotide and/or oligonucleotide, characterized in that this process includes: with the presence of a condensing agent and under the conditions of condensation reaction, the compound of Formula (2) is contacted with the compound of Formula (3) in the first liquid reaction medium to obtain the compound of Formula (4);

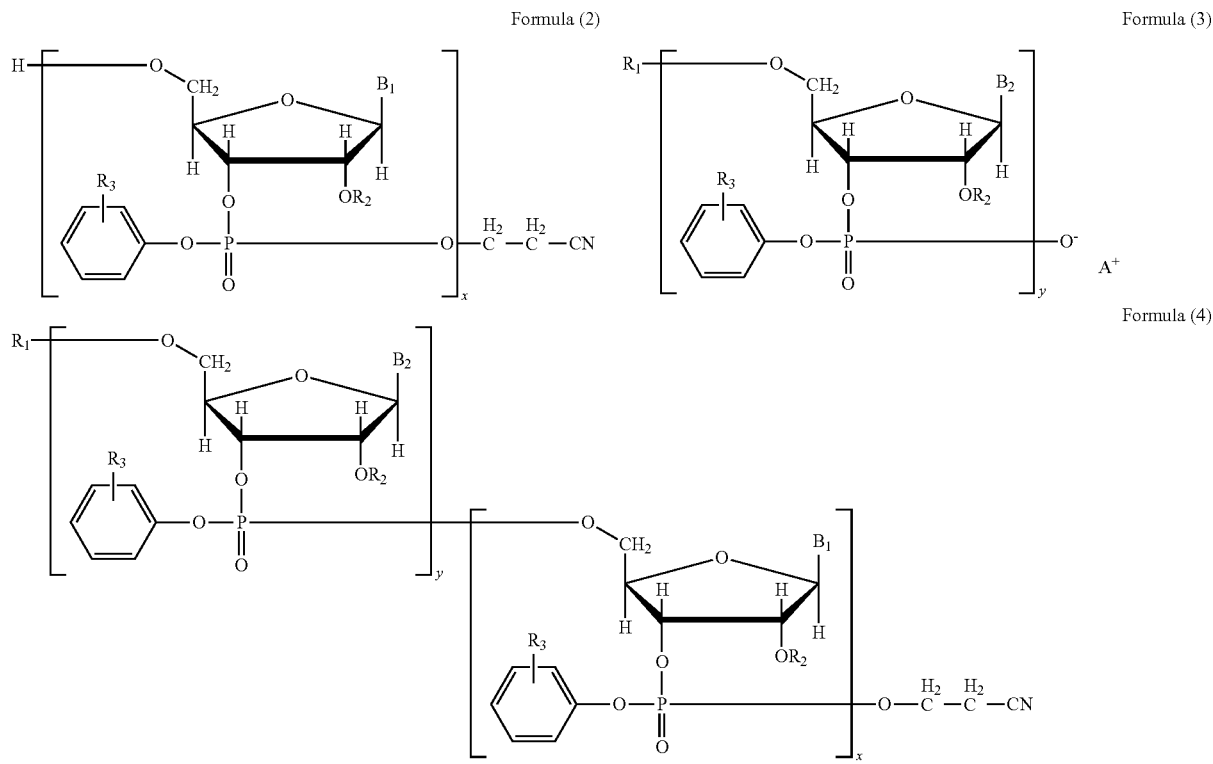

Formula (2)

Formula (3)

Formula (4)

wherein, x is an integer in the range of 0-50; y is an integer in the range of 1-50;

$B_1$ and $B_2$ represent guanine group with exocyclic amino group protected by acyl, adenine group with exocyclic amino group protected by acyl, cytosine group with exocyclic amino group protected by acyl, thymine group or uracil group, respectively, and $B_1$ and $B_2$ of each repeat unit are identical or different;

The definitions of $R_1$, $R_2$ and $R_3$ are as described in Formula (1);

$A^+$ represents trialkylammonium ion or dialkylammonium ion.

The oligonucleotide with protective group removed obtained by the process provided by the present invention may possess bioactivity and may be used for various purposes, such as: RNA interference.

The process provided by the present invention for liquid-phase synthesis of nucleotide and/or oligonucleotide includes a process for combining the protective groups of nucleotide and/or oligonucleotide. Under the precondition that 2'-OH is protected by a group with a sterically hindered silane structure, β-cyanoethyl directly protects 3' phosphate group of nucleotide and/or oligonucleotide, without using a solid-phase carrier so that the compound of Formula (4) can directly participate in the next round of synthesis after removing β-cyanoethyl, and the synthesis product is consistent with the deprotection procedure of the solid-phase synthesis process and purer.

According to the present invention, as the reaction takes place in a liquid phase, no solid-phase carrier is needed, and as multi-fold excess of the substrate is not needed, the raw material is saved and the cost is reduced. The present invention adopts protected nucleotide and/or oligonucleotide salt as a raw material, and the synthetic reaction takes place in a reaction flask or a reaction kettle without the restriction of the solid-phase carrier or synthesizer and large-scale preparation of nucleotide and/or oligonucleotide can be realized.

DETAILED DESCRIPTION OF THE EMBODIMENTS

Figure 1:
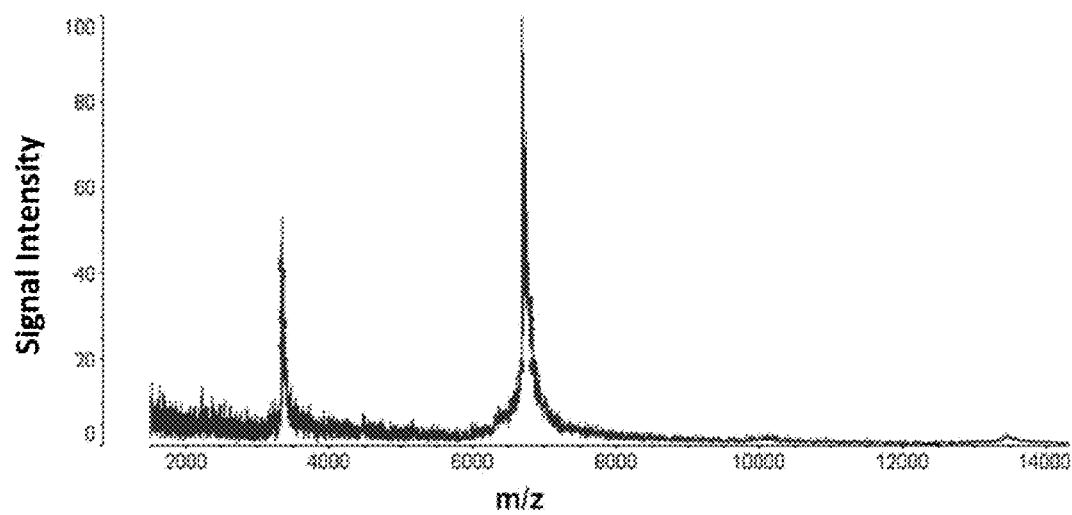
FIG. 1 is a mass spectrometry analysis chart of the deprotected henicosamer RNA CCUUGAGGCAUACUU-CAAAUU (SEQ ID NO:1) obtained in Example 1.

The present invention provides a nucleotide and/or oligonucleotide as represented by Formula (1).

In Formula (1):

R is H or $R_1$, and $R_1$ represents a protective group and may be any group that can protect 5'-OH, preferably trityl, monomethoxytrityl, 4,4'-dimethoxytritylt or trimethoxytrityl;

n may be any positive integer in theory, preferably an integer in the range of 1-100, more preferably an integer in the range of 1-50, still more preferably an integer in the range of 1-30;

B represents guanine group with exocyclic amino group protected by acyl, adenine group with exocyclic amino group protected by acyl, cytosine group with exocyclic amino group protected by acyl, thymine group or uracil group, and B of each repeat unit is identical or different.
$R_2$ represents a group with a sterically hindered silane structure.
$R_3$ represents a substituent group on the benzene ring, preferably halogen atom, nitro or methoxyl, and $R_3$ of each repeat unit may be identical or different, wherein the position of $R_3$ on the benzene ring is not limited and may be ortho-, meta- or para-position.

Wherein, when n=1, Formula (1) represents nucleotide, and when n is an integer greater than 1, Formula (1) represents oligonucleotide.

In Formula (1), the group with a steric ally hindered silane structure may be a silane group with steric hindrance and protective functions, preferably tert-butyl dimethyl silyl, phenyl dimethyl silyl, tert-butyl diphenyl silyl or triisopropyl silyl, more preferably tert-butyl dimethyl silyl, and $R_2$ of each repeat unit may be identical or different.

In Formula (1), each of the acyl as a protective group may be identical or different and may be benzoyl, isobutyryl or acetyl respectively.

In Formula (1), the halogen atom may be F, Cl, Br or I, preferably Cl or Br, more preferably Cl.

In the compound of Formula (1) provided by the present invention, when R is H, Formula (1) is equivalent to the following Formula (2) with x equal to or greater than 1; and when R is $R_1$, Formula (1) is equivalent to the following Formula (4) and when R is $R_1$, Formula (1) is equivalent to the following Formula (6).

The present invention further provides a process for liquid-phase synthesis of nucleotide and/or oligonucleotide, characterized in that this process includes: with the presence of a condensing agent and under the conditions of condensation reaction, the compound of Formula (2) is contacted with the compound of Formula (3) in the first liquid reaction medium to obtain the compound of Formula (4).

In Formula (2), (3) or (4),
x may be any non-negative integer in theory, preferably an integer in the range of 0-50, more preferably an integer in the range of 0-25, still more preferably an integer in the range of 0-15;
y may be any positive integer in theory, preferably an integer in the range of 1-50, more preferably an integer in the range of 1-25, still more preferably an integer in the range of 1-15.
$B_1$ and $B_2$ represent guanine group with exocyclic amino group protected by acyl, adenine group with exocyclic amino group protected by acyl, cytosine group with exocyclic amino group protected by acyl, thymine group or uracil group, respectively, and $B_1$ and $B_2$ of each repeat unit are identical or different. The definition of acyl is as described in Formula (1).

The definitions of $R_1$, $R_2$ and $R_3$ are as described in Formula (1);

$A^+$ represents trialkylammonium ion or dialkylammonium ion. The alkyl groups in the ion may be identical or different and each may have 1-6 carbon atoms, preferably 1-4 carbon atoms.

The condensing agents used in the condensation reaction and the conditions of the condensation reaction are known to those of ordinary skill in the art. The present invention does not have particular limitation to them. For example, the condensing agent may be one or more of 1-mesitylene-sulfonyl-triazole, 1-mesitylene-sulfonyl-(3-nitro)-triazole, 1-mesitylene-sulfonyl-tetrazole, 1-triisopropyl-phenyl-sulfonyl-triazole, 1-triisopropyl-phenyl-sulfonyl-(3-nitro)-triazole and 1-triisopropyl-phenyl-sulfonyl-tetrazole, and the first liquid reaction medium may be one or more of pyridine, dichloromethane, acetonitrile, dioxane and tetrahydrofuran;

The conditions of the condensation reaction may include: relative to 1 mol of the compound of Formula (3), when x is equal to 0, i.e.: the compound of Formula (2) is 3-hydroxypropionitrile, the amount of the compound of Formula (2) may be 1-5 mol, preferably 1.2-3 mol, more preferably 1.5-2 mol; when x is greater than or equal to 1, the amount of the compound of Formula (2) may be 0.3-1.25 mol.

Relative to 1 mol of the compound of Formula (3), the amount of the condensing agent may be 2-20 mol, preferably 2-5 mol.

Relative to 1 mol of the compound of Formula (3), the amount of the first liquid reaction medium may be 2-50 L, preferably 2-30 L.

The reaction temperature may be 0-50° C., preferably 20-40° C.; the reaction time may be 0.5-100 h, preferably 1-10 h.

After the condensation reaction is completed, the condensation reaction may be terminated and the product is separated. The process for terminating the condensation reaction and the process for separating the product are known to those of ordinary skill in the art. The present invention does not have particular limitation to them.

For example, the process for terminating the condensation reaction may be: mixing the reaction solution with water at 0-15° C. for 5-30 min. Relative to 1 L of the first liquid reaction medium, the amount of water may be 0.05-0.2 L.

The process for terminating the condensation reaction may also be: mixing the reaction solution with a saturated sodium bicarbonate solution, and keeping stirring the mixed solution at 0-50° C. for 5-10 min. The volume ratio between the saturated sodium bicarbonate solution and the first liquid reaction medium may be 0.05-0.2:1.

When the compound of Formula (4) needs to take the following displacement reaction, the separation process may include: removing the solvent from the reaction solution by rotary evaporation after the reaction is terminated, dissolving remnant in an organic solvent, regulating pH value to 3-5 with an acid and washing it with water once or multiple times. Relative to 1 L of the first liquid reaction medium, the amount of the organic solvent is 2-20 L and the amount of the water for wash is 2-20 L. After the organic phase is dried with anhydrous sodium sulfate, the solvent is removed by rotary evaporation again and the product is obtained after separation by an ordinary-pressure column. The organic solvent may be one or more of dichloromethane, trichloromethane and ethyl acetate. The acid may be oxalic acid and/or acetic acid with a concentration of 1-10 wt %.

When the compound of Formula (4) needs to be carried out the following hydrolysis reaction or removed all protective groups, the separation process may include: removing the solvent from the reaction solution by rotary evaporation after the reaction is terminated, mixing the remnant with an organic solvent, adding a saturate sodium bicarbonate solution to wash it, and drying, filtering, concentrating and separating in an ordinary-pressure column the organic phase to obtain the product. The organic solvent may be one or more of dichloromethane, trichloromethane and ethyl acetate. The volume ratio between the organic solvent and the first liquid reaction medium may be 2-20:1. The washing may be conducted once or multiple times. The ratio between the total volume of the saturated sodium bicarbonate solution used in washing and the volume of the first liquid reaction medium may be 2-20:1. The processes of drying, filtration, concentration and separation in an ordinary-pressure column are known to those skilled in the art, so they are not further described here.

Therefore, according to the first embodiment of the present invention, the process provided by the present invention for liquid-phase synthesis of nucleotide and/or oligonucleotide may further includes: in the second liquid reaction medium, with the presence of trialkylamine or dialkylamine and under the conditions of hydrolysis reaction, the compound of Formula (4) is contacted with water and undergoes hydrolysis reaction to remove β-cyanoethyl and obtain a hydrolytic product with β-cyanoethyl removed.

Wherein, the conditions of the hydrolysis reaction may include: relative to 1 mol of the compound of Formula (4), the amount of trialkylamine or dialkylamine may be 1-200 mol, preferably 40-150 mol; the amount of the second liquid reaction medium may be 5-50 L, preferably 5-40 L; the amount of water may be 2-20 L, preferably 2-15 L; the reaction temperature may be 0-50° C., preferably 10-35° C.; the reaction time may be 0.25-2 h, preferably 0.25-1 h.

Wherein, the preferred second liquid reaction medium is pyridine and/or acetonitrile.

The alkyl groups in the trialkylamine or dialkylamine are identical or different, and each has 1-6 carbon atoms. For example, the trialkylamine may be one or more of trimethylamine, triethylamine and diisopropylethylamine, and the dialkylamine may be one or more of dimethylamine, diethylamine and diisopropylamine.

After the hydrolysis reaction is completed, the product obtained after the hydrolysis reaction may be separated. The separation process is known to those of ordinary skill in the art and not particularly limited by the present invention. For example, this separation process may include: the solvent of the reaction solution is removed by rotary evaporation, then the remnant is dissolved in an organic solvent, a washing solution is added to wash it, an organic phase is obtained through liquid division and the solvent is removed by rotary evaporation after drying with anhydrous sodium sulfate to obtain the product. The organic solvent may be one or more of dichloromethane, trichloromethane or ethyl acetate. The volume ratio between the organic solvent and the second liquid reaction medium may be 1-10:1. The wash solution may be 0.1-1 mol/L triethylamine bicarbonate (TEAB) water solution or saturated sodium bicarbonate solution. The washing may be conducted once or a number of times. The ratio between the total volume of the TEAB water solution used in washing and the second liquid reaction medium may be 1-10:1.

Then, the separated hydrolytic product is used as the compound of Formula (3) and undergoes the said condensation reaction with the compound of Formula (2) again.

According to the second embodiment of the present invention, the process provided by the present invention for liquid-phase synthesis of nucleotide and/or oligonucleotide may further includes: in the third liquid reaction medium, with the presence of an organic acid and under the conditions of displacement reaction, the $R_1$ group in the compound of Formula (4) is replaced with H to obtain a product generated by replacing $R_1$ group with H.

Wherein, the conditions of the displacement reaction may be: relative to 1 mol of the compound of Formula (4), the amount of the organic acid may be 2-20 mol, preferably 2-10 mol; the amount of the third liquid reaction medium may be 10-150 L, preferably 10-130 L; the reaction temperature may be –10° C. to 40° C., preferably –10° C. to 30° C.; the reaction time may be 1-60 min, preferably 1-20 min; the organic acid is preferably one or more of methyl benzenesulfonic acid, benzenesulfonic acid, trichloroacetic acid, dichloroacetic acid and trifluoroacetic acid; the third liquid reaction medium may be one or more of dichloromethane, trichloromethane, acetonitrile and methanol.

Wherein, after the displacement reaction is completed, a product generated by replacing $R_1$ group with H may be separated. The separation process is known to those of ordinary skill in the art and not particularly limited by the present invention. For example, this separation and purification process may include: using aqueous alkali to neutralize the mixture obtained from the displacement reaction, obtaining an organic solvent through liquid division, washing it with aqueous alkali once or a number of times and drying, filtering, concentrating and separating in an ordinary-pressure column the organic phase to obtain a purified product after the displacement reaction. Relative to 1 L of the third liquid reaction medium, the amount of the aqueous alkali used in washing may be 0.2-1 L. The aqueous alkali may be a saturated sodium bicarbonate water solution, a saturated potassium bicarbonate water solution or a saturated sodium carbonate solution. The processes of drying, filtration, concentration and separation in an ordinary-pressure column are known to those skilled in the art, so they are not further described here.

Then, the separated product generated by replacing $R_1$ group with H may be used as the compound of Formula (2) and undergoes the said condensation reaction with the compound of Formula (3) again.

When x is greater than or equal to 1, the compound of Formula (2) may be obtained by replacing $R_1$ group in the compound of Formula (6) with H.

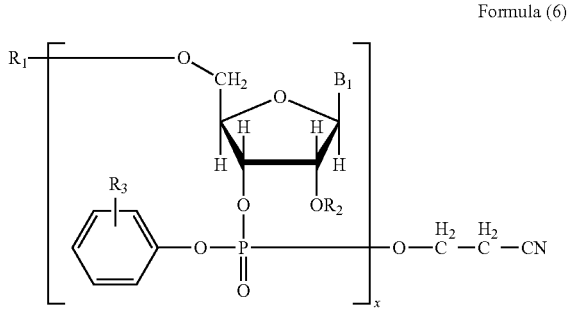

Formula (6)

Where, the definitions of x, $B_1$, $R_2$, $R_3$ are as described in Formula (2), but x is greater than or equal to 1; the definition of $R_1$ is as described in Formula (3).

The process for replacing the $R_1$ group in the compound of Formula (6) with H is identical as the process for replacing the $R_1$ group in the compound of Formula (4) with H except that the compound of Formula (6) is adopted instead of the compound of Formula (4).

The process for preparing the compound of Formula (6) includes: using the compound of Formula (5) as the compound of Formula (3) and taking the said condensation reaction with the compound of Formula (2) with x equal to 0, i.e.: 3-hydroxypropionitrile.

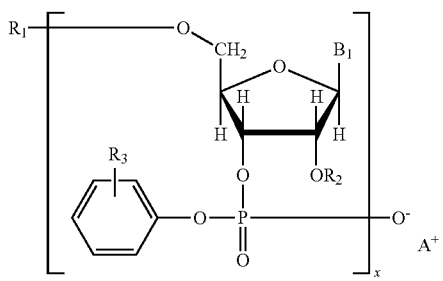

Formula (5)

Wherein, the definitions of x, $B_1$, $R_2$ and $R_3$ are as described in Formula (2), but x is greater than or equal to 1; the definitions of $R_1$ and $A^+$ are as described in Formula (3).

When y in Formula (3) is equal to x in Formula (5), Formula (3) is equivalent to Formula (5).

The processes for preparing the compound of Formula (3) and/or the compound of Formula (5) have been recorded in details in the disclosed document PCT/CN2009/074101 and will not be further described here.

In respect to long-segment small nucleic acid, the present invention provides a modular synthesis strategy. For example, a henicosamer nucleic acid chain is split into four parallel segments of pentamer to hexamer, which will be further split into more parallel short segments of dimer to trimer. After synthesis of the short dimer segments, the trimers may be synthesized into n-mer (n is the target length) oligonucleotide chain. Therefore, theoretically, by the process provided by the present invention, the oligonucleotide chains of any length can be synthesized. The embodiments below describe the present invention by only taking dotetracontamer in the longest for example.

By the process provided by the present invention, fully protected nucleotide and/or oligonucleotide of Formula (4) may be synthesized. All the protective groups of the fully protected nucleotide and/or oligonucleotide include: acyl, β-cyanoethyl, group of Formula (7), $R_1$ and $R_2$ in Formula (4),

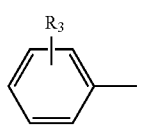

Formula (7)

wherein, the definition of $R_3$ is the same as that of Formula (4).

All the protective groups in the fully protected nucleotide and/or oligonucleotide may be removed in two steps:

Step 1: The compound of Formula (4) is contacted with aqua ammonia in the fourth liquid reaction medium under the first deprotection reaction conditions to remove one proportion of protective groups to obtain a product with one proportion of protective groups removed. The said one proportion of protective groups refer to acyl, β-cyanoethyl and group of Formula (7) in Formula (4).

Wherein, the fourth liquid reaction medium may be one or more of dioxane, acetonitrile, pyridine, ethanol and methanol; the first deprotection reaction conditions include: relative to 1 g of the compound of Formula (4), the amount of aqua ammonia may be 0.02-0.5 L, preferably 0.05-0.3 L; the amount of the fourth liquid reaction medium may be 0.01-0.2 L, preferably 0.02-0.1 L; the reaction temperature may be 10-60° C., preferably 10-30° C.; the reaction time may be 5-100 h, preferably 10-60 h; the concentration of the aqua ammonia is 25-28 mass %. After the first deprotection reaction is completed, concentration under reduced pressure may be adopted to remove the solvent till fully dry. The obtained solid is a product with one proportion of protective groups removed.

Step 2: in the fifth liquid reaction medium, under the second deprotection reaction conditions, the product with one proportion of protective groups removed is contacted with triethylamine trihydrofluoric acid (TEA.3HF) to remove the remaining protective groups to obtain a product with all protective groups removed. The said remaining protective groups are $R_1$ and $R_2$. The definitions of $R_1$ and $R_2$ are the same as those in Formula (4).

Wherein, the fifth liquid reaction medium is dimethyl sulfoxide; the second deprotection reaction conditions include: relative to 1 g of the product with some protective groups removed, the amount of TEA.3HF is 0.002-0.05 L, preferably 0.005-0.03 L; the amount of the fifth liquid reaction medium is 0.002-0.05 L, preferably 0.005-0.03 L; the reaction temperature is 40-85° C., preferably 50-75° C.; the reaction time is 1-5 h, preferably 2-4 h.

After the deprotection reaction is completed, the product obtained from the deprotection reaction may be separated. The separation process is known to those of ordinary skill in the art and not particularly limited by the present invention. For example, the separation process may be: adding pre-cooled normal butanol into the reaction solution, settling nucleotide and/or oligonucleotide and collecting the precipitate by centrifuge to obtain a crude product of nucleotide and/or oligonucleotide.

The obtained crude product of nucleotide and/or oligonucleotide may be purified. The purification process is known to those of ordinary skill in the art and is not particularly limited by the present invention. For example, the purification process may be: injecting the crude product of nucleotide and/or oligonucleotide into reverse phase octadecyl silane bonding silica gel packing (ODS) chromatograph, collecting the eluate and freezing and drying the eluate to obtain the target product.

The oligonucleotide with protective groups removed obtained by the process provided by the present invention is bioactive and may be used for various purposes, such as: RNA interference.

The volume of the gases and liquids used in the present invention refers to the volume at one standard atmospheric pressure and 20° C.

Below the present invention is described in details by the embodiments, but the scope of the present invention is not limited to the examples in the embodiments.

The raw materials used in the embodiments are obtained by the following processes:

Four types of protected ribonucleotides, including adenine ribonucleotide (A), uracil ribonucleotide (U), cytosine ribonucleotide (C) and guanine ribonucleotide (G) where benzoyl protects the exocyclic amino of the base, tert-butyl dimethyl silyl protects 2'OH, and 4,4'-dimethoxytrityl protects 5'OH; all of the four types of protected nucleotides are purchased from Shanghai GenePharma Co., Ltd.;

Triethylamine: purchased from Tianjin Beifang Tianyi Chemical Reagent Factory;

1,2,4-triazole: purchased from Alfa Aesar;

2-phenyl dichlorophosphate: purchased from Alfa Aesar;

1-mesitylene-sulfonyl-(3-nitro)-triazole (MSNT): purchased from Sigma Aldrich.

Example 1

This example synthesizes oligonucleotide.

Synthesis target: henicosamer fully protected oligoribo-oligonucleotide

Sequence: DMTr[CCUUGAGGCAUACUUCAAAUU]OE (SEQ ID NO:2)

Notes: The four letters A, U, C and G in the square brackets represent four types of protected ribonucleotides. Their exocyclic amino groups are protected by benzoyl. 2'OHs are protected by tert-butyl dimethyl silyl. The protective groups: phosphate and phenol phosphate between bases are omitted.

The group on the left of the square bracket represents the protective group at the terminal of 5', which is 4,4'-dimethoxytrityl (DMTr), and may also be OH.

The group on the right of the square bracket represents the protective group at the terminal of 3', which is propionitrile phosphate (OE), and may also be phosphate (PO$^-$).

Figure 4:
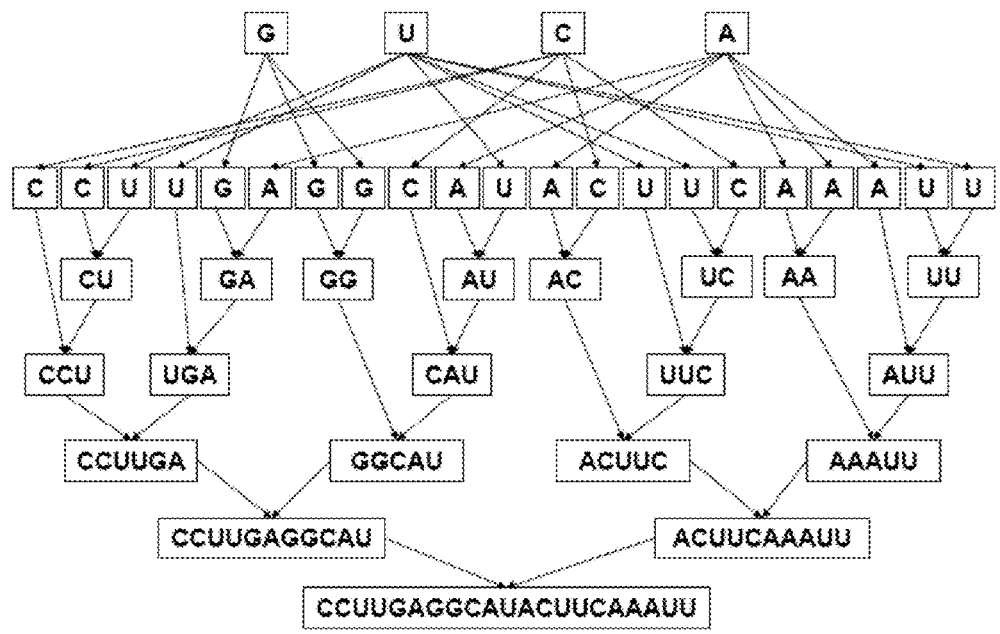
FIG. 4 is a schematic of the synthesis strategy of Example 1.

The synthesis in this embodiment includes 30 steps according to the synthesis strategy represented by FIG. 4.

(1) Synthesize monomer DMTr[A]PO$^-$ of the compound of Formula (3):

1,2,4-triazole (13.8 g, 200 mmol) and anhydrous pyridine (31.6 g, 400 mmol) are added to a 1 L round-bottomed flask and dissolved in 130 ml of dichloromethane. 65 ml of 2-phenyl dichlorophosphate (19.6 g, 80 mmol) dichloromethane solution is dropwise added under the condition of an ice bath and reacts while stirred for 0.5 h. Then 150 ml of protected adenine ribonucleotide (39.4 g, 50 mmol) dichloromethane solution is dropwise added and reacts while stirred under the condition of an ice bath for 2 h. Then 150 ml of 1M TEAB solution is added. The stirring is continued for 10 min. After washing with 1M TEAB solution three times (90 ml a time), all organic phase is dried with anhydrous Na$_2$SO$_4$. After filtration and removal of the solvent by rotary evaporation, 54.0 g of the product is obtained. The yield is 100%. The yield is the percentage of the weight of the product to the theoretical output calculated based on the protected adenine ribonucleotide.

The $^{31}$PNMR spectrum of the product is detected to obtain $^{31}$PNMR (CDCl$_3$, 121M) δ-6.09, which is consistent with the range of the theoretical values of $^{31}$PNMR of pentavalent phosphodiester (refer to literature Tetrahedron, 1980 (36), page 3075-3085), proving this product indeed has the structure of Formula (3).

The M$^-$ of the product detected by ESI-MS is 976.2915, which is fully consistent with the theoretical value of M$^-$ of the target product, proving this product indeed has the structure of Formula (3).

(2) Synthesize Monomer DMTr[U]PO$^-$ of the Compound of Formula (3):

It is synthesized by a process same as Step (1) except that protected uracil ribonucleotide substitutes protected adenine ribonucleotide.

The $^{31}$PNMR spectrum and M$^-$ of the product are detected. They are fully consistent with the theoretical values of $^{31}$PNMR spectrum and M$^-$ of the target product, proving this product indeed has the structure of Formula (3).

(3) Synthesize monomer DMTr[G]PO$^-$ of the compound of Formula (3):

It is synthesized by a process same as Step (1) except that protected guanine ribonucleotide substitutes protected adenine ribonucleotide.

The $^{31}$PNMR spectrum and M$^-$ of the product are detected. They are fully consistent with the theoretical values of $^{31}$PNMR spectrum and M$^-$ of the target product, proving this product indeed has the structure of Formula (3).

(4) Synthesize monomer DMTr[C]PO$^-$ of the compound of Formula (3):

It is synthesized by a process same as Step (1) except that protected cytosine ribonucleotide substitutes protected adenine ribonucleotide.

The $^{31}$PNMR spectrum and M$^-$ of the product are detected. They are fully consistent with the theoretical values of $^{31}$PNMR spectrum and M$^-$ of the target product, proving this product indeed has the structure of Formula (3).

(5) Synthesize the Monomer HO[A]OE of the Compound of Formula (2):

DMTr[A]PO$^-$ (17.3 g, 16 mmol) obtained in Step (1) is added to a 250 ml round-bottomed flask and dissolved in anhydrous pyridine (100 ml). 3-hydroxypropionitrile (1.70 g, 24 mmol) is added and then MSNT (13.3 g, 44.8 mmol) is added. The reaction lasts 2 h at 20° C. After thin layer chromatography (TLC) indicates thorough reaction, water (10 ml) is added to terminate the reaction. After the solvent is removed by rotary evaporation, it is redissolved in CH$_2$Cl$_2$ (200 ml). An appropriate amount of 5 wt % oxalic acid water solution is added to regulate pH value to 3-4. An organic phase is obtained through liquid division. It is washed with water (100 ml) once. The organic phase is dried with anhydrous Na$_2$SO$_4$. Then the solvent is removed by rotary evaporation again. 2 wt % para-toluenesulfonic acid (TsOH) CH$_2$Cl$_2$/CH$_3$OH (v:v=7:3) solution (700 ml) is added and violently stirred at 0° C. for 5 min.

Then the solution is immediately neutralized with a saturated NaHCO$_3$ solution. An organic phase is obtained through liquid division. It is washed with a saturated NaHCO$_3$ solution (300 ml) once again. After the organic phase is dried with anhydrous Na$_2$SO$_4$, the solvent is removed. After purification by column chromatography (the eluent is CH$_2$Cl$_2$/CH$_3$OH (v:v=10:1)), 10.9 g of the product is obtained. The yield is 93.4%. The yield is the percentage of the weight of the product to the theoretical output calculated based on DMTr[A]PO$^-$.

The $^{31}$PNMR spectrum of the product is detected to obtain $^{31}$PNMR (CDCl$_3$, 121M) δ-7.66, -7.79, which are consistent with the theoretical value of $^{31}$PNMR of pentavalent phosphodiester, proving this product indeed has the structure of Formula (2).

The M$^-$ of the product detected by ESI-MS is 728.1956, which is fully consistent with the theoretical value of M$^-$ of the target product, proving this product indeed has the structure of Formula (2).

(6) Synthesize monomer HO[U]OE of the compound of Formula (2):

It is synthesized by a process same as Step (5) except that DMTr[U]PO$^-$ obtained in Step (2) substitutes DMTr[A]PO$^-$ obtained in Step (1).

The $^{31}$PNMR spectrum and M$^-$ of the product are detected. They are fully consistent with the theoretical values of $^{31}$PNMR spectrum and M$^-$ of the target product, proving this product indeed has the structure of Formula (2).

(7) Synthesize monomer HO[G]OE of the compound of Formula (2):

It is synthesized by a process same as Step (5) except that DMTr[G]PO$^-$ obtained in Step (3) substitutes DMTr[A]PO$^-$ obtained in Step (1).

The $^{31}$PNMR spectrum and M$^-$ of the product are detected. They are fully consistent with the theoretical values of $^{31}$PNMR spectrum and M$^-$ of the target product, proving this product indeed has the structure of Formula (2).

(8) Synthesize Monomer HO[C]OE of the Compound of Formula (2):

It is synthesized by a process same as Step (5) except that DMTr[C]PO$^-$ obtained in Step (4) substitutes DMTr[A]PO$^-$ obtained in Step (1).

The $^{31}$PNMR spectrum and M$^-$ of the product are detected. They are fully consistent with the theoretical values of $^{31}$PNMR spectrum and M$^-$ of the target product, proving this product indeed has the structure of Formula (2).

(9) Synthesize Dimer DMTr[AA]OE of Formula (4):

DMTr[A]PO$^-$ (2.59 g, 2.40 mmol) obtained in Step (1) and HO[A]OE (1.46 g, 2.00 mmol) obtained in Step (5) are added to a 100 ml round-bottomed flask. After they are dissolved in 10 ml of anhydrous pyridine, MSNT (1.66 g, 5.60 mmol) is added. The reaction lasts 2 h at room temperature. After TLC indicates thorough reaction, 2 ml of saturated NaHCO$_3$ solution is added to terminate the reaction. After the solvent is removed by rotary evaporation, the remnant is redissolved in 50 ml of CH$_2$Cl$_2$ and washed with a saturated NaHCO$_3$ solution twice (30 ml per time). After the organic phase is dried with anhydrous Na$_2$SO$_4$, the solvent is removed. After purification by column chromatography (the eluent is CH$_2$Cl$_2$/CH$_3$OH (v:v=10:1)), 3.26 g of the product is obtained.

The $^{31}$PNMR spectrum of the product is detected to obtain $^{31}$PNMR (CDCl$_3$, 121M) δ-7.36, −7.46, −7.55, −7.90, which are consistent with the theoretical value of $^{31}$PNMR of pentavalent phosphodiester, proving this product indeed has the structure of Formula (4).

The M$^-$ of the product detected by ESI-MS is 1687.64, which is consistent with the theoretical value of M$^-$ of the target product, proving this product indeed has the structure of Formula (4).

(10) Synthesize dimer DMTr[AA]PO$^-$:

DMTr[AA]OE purified in Step (9) is dissolved in 60 ml of pyridine/triethylamine/water (v:v:v=3:1:1) and stirred at room temperature for 30 min. After TLC indicates thorough reaction, the solvent is removed from the reaction solution by rotary evaporation. Then the remnant is dissolved in 100 ml of CH$_2$Cl$_2$ again and washed with 1M TEAB solution three times (50 ml per time). An organic phase is obtained through liquid division. The solvent is removed from the organic phase after drying of anhydrous Na$_2$SO$_4$ to obtain 3.20 g of the product. The total yield of the reactions in Step (9) and Step (10) is 93.9%. The yield is the percentage of the weight of the product to the theoretical output calculated based on HO[A]OE.

The $^{31}$PNMR spectrum and M$^-$ of the product are detected. They are fully consistent with the theoretical values of $^{31}$PNMR spectrum and M$^-$ of the target compound, proving this product indeed has the structure of Formula (3).

(11) Synthesize Dimer DMTr[GG]PO$^-$:

It is synthesized by a process same as Step (9) and Step (10) except that DMTr[G]PO$^-$ obtained in Step (3) substitutes DMTr[A]PO$^-$ obtained in Step (1) and HO[G]OE obtained in Step (7) substitutes HO[A]OE obtained in Step (5).

The $^{31}$PNMR spectrum and M$^-$ of the product are detected. They are fully consistent with the theoretical values of $^{31}$PNMR spectrum and M$^-$ of the target compound, proving this product indeed has the structure of Formula (3).

(12) Synthesize dimer DMTr[AC]PO$^-$:

It is synthesized by a process same as Step (9) and Step (10) except that HO[C]OE obtained in Step (8) substitutes HO[A]OE obtained in Step (5).

The $^{31}$PNMR spectrum and M$^-$ of the product are detected. They are fully consistent with the theoretical values of $^{31}$PNMR spectrum and M$^-$ of the target compound, proving this product indeed has the structure of Formula (3).

(13) Synthesize Dimer HO[AU]OE:

DMTr[A]PO$^-$ (16.2 g, 15 mmol) obtained in Step (1) is added to a 500 ml round-bottomed flask. After they are dissolved in 100 ml of anhydrous pyridine, HO[U]OE (7.53 g, 12.5 mmol) obtained in Step (6) is added. MSNT (10.4 g, 35 mmol) is added. The reaction lasts 2 h at room temperature. After TLC indicates thorough reaction, 10 ml of water is added to terminate the reaction. After the solvent is removed by rotary evaporation, the remnant is redissolved in 300 ml of CH$_2$Cl$_2$. An appropriate amount of 5% oxalic acid water solution is added to regulate pH value to 3-4. An organic phase is obtained through liquid division. It is washed with 150 ml of water once. The organic phase is dried with anhydrous Na$_2$SO$_4$. Then the solvent is removed by rotary evaporation again. 2 wt % toluenesulfonic acid (TsOH) CH$_2$Cl$_2$/CH$_3$OH (v:v=7:3) solution (700 ml) is added and violently stirred at 0° C. for 5 min.

Then the solution is immediately neutralized with a saturated NaHCO$_3$ solution. An organic phase is obtained through liquid division. It is washed with a saturated NaHCO$_3$ solution (300 ml) once again. After the organic phase is dried with anhydrous Na$_2$SO$_4$, the solvent is removed. After purification by column chromatography (the eluent is CH$_2$Cl$_2$/CH$_3$OH (v:v=10:1)), 12.9 g of the product is obtained. The yield is 81.8%. The yield is the percentage of the weight of the product to the theoretical output calculated based on HO[U]OE.

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).

(14) Synthesize Dimer HO[CU]OE:

It is synthesized by a process same as Step (13) except that DMTr[C]PO$^-$ obtained in Step (4) substitutes DMTr[A]PO$^-$ obtained in Step (1).

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).

(15) Synthesize Dimer HO[GA]OE:

It is synthesized by a process same as Step (13) except that DMTr[G]PO$^-$ obtained in Step (3) substitutes DMTr[A]PO$^-$ obtained in Step (1) and HO[A]OE obtained in Step (5) substitutes HO[U]OE obtained in Step (6).

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).

(16) Synthesize Dimer HO[UC]OE:

It is synthesized by a process same as Step (13) except that DMTr[U]PO$^-$ obtained in Step (2) substitutes DMTr[A]PO$^-$ obtained in Step (1) and HO[C]OE obtained in Step (8) substitutes HO[U]OE obtained in Step (6).

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).

(17) Synthesize Dimer HO[UU]OE:

It is synthesized by a process same as Step (13) except that DMTr[U]PO$^-$ obtained in Step (2) substitutes DMTr[A]PO$^-$ obtained in Step (1).

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).

(18) Synthesize Trimer DMTr[CCU]PO$^-$:

DMTr[C]PO$^-$ (3.17 g, 3.00 mmol) obtained in Step (4) and HO[CU]OE (3.09 g, 2.50 mmol) obtained in Step (14) are added to a 100 ml round-bottomed flask and dissolved in 20 ml of anhydrous pyridine. MSNT (2.08 g, 7.00 mmol) is added. The reaction lasts 2 h at room temperature. After TLC indicates thorough reaction, 2 ml of saturated NaHCO$_3$ solution is added to terminate the reaction. After the solvent is removed by rotary evaporation, the remnant is redissolved in 100 ml of CH$_2$Cl$_2$ and washed with 50 ml of saturated NaHCO$_3$ solution. An organic phase is obtained through liquid division. After the organic phase is dried with anhydrous Na$_2$SO$_4$, the solvent is removed. After purification by column chromatography (the eluent is CH$_2$Cl$_2$/CH$_3$OH (v:v=10:1)), a purified product is obtained. The purified product is dissolved in 60 ml of pyridine/triethylamine/water (v:v:v=3:1:1). The solution is stirred for 30 min at room temperature. After TLC indicates thorough reaction, the solvent is removed from the reaction solution by rotary evaporation. The remnant is redissolved in 100 ml of CH$_2$Cl$_2$ and washed with 1M TEAB solution three times (50 ml per time). An organic phase is separated. After it is dried with anhydrous Na$_2$SO$_4$, the solvent is removed. 4.89 g of the product is obtained. The yield is 88.5%. The yield is the percentage of the weight of the product to the theoretical output calculated based on HO[CU]OE.

The $^{31}$PNMR spectrum and M$^-$ of the product are detected. They are fully consistent with the theoretical values of $^{31}$PNMR spectrum and M$^-$ of the target compound, proving this product indeed has the structure of Formula (3).

(19) Synthesize Trimer HO[UGA]OE:

DMTr[U]PO$^-$ (10.0 g, 10.5 mmol) obtained in Step (2) and HO[GA]OE (12.0 g, 8.76 mmol) obtained in Step (15) are added to a 250 ml round-bottomed flask and dissolved in 50 ml of anhydrous pyridine. MSNT (7.31 g, 24.5 mmol) is added by three times. The reaction lasts 2 h at room temperature. After TLC indicates thorough reaction, 5 ml of water is added to terminate the reaction. After the solvent is removed by rotary evaporation, the remnant is redissolved in 200 ml of CH$_2$Cl$_2$. An appropriate amount of 5% oxalic acid water solution is added to regulate pH value to 3-4. An organic phase is separated. It is washed with 100 ml of water once. The organic phase is dried with anhydrous Na$_2$SO$_4$. Then the solvent is removed by rotary evaporation again. 550 ml of 2% TsOH CH$_2$Cl$_2$/CH$_3$OH (v:v=7:3) solution is added and violently stirred at 0° C. for 5 min. Then the solution is immediately neutralized with a saturated NaHCO$_3$ solution. An organic phase is separated. It is washed with 200 ml of saturated NaHCO$_3$ solution once. After the organic phase is dried with anhydrous Na$_2$SO$_4$, the solvent is removed. After purification by column chromatography (the eluent is CH$_2$Cl$_2$/CH$_3$OH (v:v=10:1)), 13.0 g of the product is obtained. The yield is 78.0%. The yield is the percentage of the weight of the product to the theoretical output calculated based on HO [GA]OE.

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).

(20) Synthesize Trimer HO[CAU]OE:

It is synthesized by a process same as Step (19) except that DMTr[C]PO$^-$ obtained in Step (4) substitutes DMTr[U]PO$^-$ obtained in Step (2) and HO[AU]OE obtained in Step (13) substitutes HO[GA]OE obtained in Step (15).

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).

(21) Synthesize Trimer HO[UUC]OE:

It is synthesized by a process same as Step (19) except that HO[UC]OE obtained in Step (16) substitutes HO[GA]OE obtained in Step (15).

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).

(22) Synthesize Trimer HO[AUU]OE:

It is synthesized by a process same as Step (19) except that DMTr[A]PO$^-$ obtained in Step (1) substitutes DMTr[U]PO$^-$ obtained in Step (2) and HO[UU]OE obtained in Step (17) substitutes HO[GA]OE obtained in Step (15).

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).

(23) Synthesize Hexamer DMTr[CCUUGA]PO$^-$:

DMTr[CCU]PO$^-$ (4.18 g, 1.89 mmol) obtained in Step (18) and HO[UGA]OE (3.00 g, 1.58 mmol) obtained in Step (19) are added to a 100 ml round-bottomed flask and dissolved in 10 ml of anhydrous pyridine. MSNT (1.31 g, 4.42 mmol) is added. The reaction lasts 3 h at room temperature. After TLC indicates thorough reaction, 2 ml of saturated NaHCO$_3$ solution is added to terminate the reaction. After the solvent is removed by rotary evaporation, the product is purified by column chromatography (the eluent is CH$_2$Cl$_2$/CH$_3$OH (v:v=10:1)). The purified product is dissolved in 60 ml of pyridine/triethylamine/water (v:v:v=3:1:1). The solution is stirred at room temperature for 30 min. After TLC indicates thorough reaction and the solvent is removed by rotary evaporation, the remnant is redissolved in 100 ml of CH$_2$Cl$_2$ and washed with 1M TEAB solution three times (50 ml per time). An organic phase is separated. After it is dried with anhydrous Na$_2$SO$_4$, the solvent is removed to obtain 5.00 g of the product. The yield is 79.3%. The yield is the percentage of the weight of the product to the theoretical output calculated based on HO[UGA]OE.

The $^{31}$PNMR spectrum and M$^-$ of the product are detected. They are fully consistent with the theoretical values of $^{31}$PNMR spectrum and M$^-$ of the target compound, proving this product indeed has the structure of Formula (3).

(24) Synthesize Pentamer DMTr[ACUUC]PO$^-$:

It is synthesized by a process same as Step (23) except that DMTr[AC]PO$^-$ obtained in Step (12) substitutes DMTr[CCU]PO$^-$ obtained in Step (18) and HO[UUC]OE obtained in Step (21) substitutes HO[UGA]OE obtained in Step (19).

The $^{31}$PNMR spectrum and M$^-$ of the product are detected. They are fully consistent with the theoretical values of $^{31}$PNMR spectrum and M$^-$ of the target compound, proving this product indeed has the structure of Formula (3).

(25) Synthesize Pentamer HO[GGCAU]OE:

DMTr[GG]PO$^-$ (5.72 g, 3.36 mmol) obtained in Step (11) and HO[CAU]OE (5.30 g, 2.80 mmol) obtained in Step (20) are added to a 250 ml round-bottomed flask and dissolved in 15 ml of anhydrous pyridine. MSNT (2.34 g, 7.84 mmol) is added. The reaction lasts 2 h at room temperature. After TLC indicates thorough reaction, 1.5 ml of water is added to terminate the reaction. After the solvent is removed by rotary evaporation, the remnant is redissolved in 100 ml of CH$_2$Cl$_2$. An appropriate amount of 5% oxalic acid water solution is added to regulate pH value to 3-4. An organic phase is separated and washed with 50 ml of water once. The organic phase is dried with anhydrous Na$_2$SO$_4$. The solvent is removed by rotary evaporation again. 170 ml of 2% TsOH CH$_2$Cl$_2$/CH$_3$OH (v:v=7:3) solution is added and violently stirred at 0° C. The solution is immediately neutralized with a saturated NaHCO$_3$ solution. An organic phase is separated. It is washed with 80 ml of saturated NaHCO$_3$ solution once. After the organic phase is dried with anhydrous Na$_2$SO$_4$, the solvent is removed. After purification by column chromatography (the eluent is CH$_2$Cl$_2$/CH$_3$OH (v:v=10:1)), 5.3 g of the product is obtained. The yield is 59.6%. The yield is the percentage of the weight of the product to the theoretical output calculated based on HO[CAU]OE.

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).

(26) Synthesize Pentamer HO[AAAUU]OE:

It is synthesized by a process same as Step (25) except that DMTr[AA]PO$^-$ obtained in Step (10) substitutes DMTr[GG]PO$^-$ obtained in Step (11) and HO[UUC]OE obtained in Step (22) substitutes HO[CAU]OE obtained in Step (20).

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).

(27) Synthesize undecamer DMTr[CCUUGAGGCAU]PO$^-$ (SEQ ID NO:3):

DMTr[CCUUGA]PO$^-$ (4.86 g, 1.20 mmol) obtained in Step (23) and HO[GGCAU]OE (3.18 g, 1.0 mmol) obtained in Step (25) are added to a 100 ml round-bottomed flask and dissolved in 10 ml of anhydrous pyridine. MSNT (0.83 g, 2.80 mmol) is added. The reaction lasts 4 h at room temperature. After TLC indicates thorough reaction, 1 ml of saturated NaHCO$_3$ solution is added to terminate the reaction. 100 ml of CH$_2$Cl$_2$ is added. It is washed with 50 ml of saturated NaHCO$_3$ solution once and with 50 ml of water once. It is dried with anhydrous Na$_2$SO$_4$. The solvent is removed by rotary evaporation. After purification by column chromatography (the eluent is CH$_2$Cl$_2$/CH$_3$OH (v:v=10:1)), the purified product is dissolved in 40 ml of pyridine/triethylamine/water (v:v:v=3:1:1). The solution is stirred at room temperature for 30 min. After TLC indicates thorough reaction and the solvent is removed by rotary evaporation, the remnant is redissolved in 100 ml of CH$_2$Cl$_2$ and washed with 1M TEAB solution three times (50 ml per time). An organic phase is separated. After it is dried with anhydrous Na$_2$SO$_4$, the solvent is removed to obtain 2.89 g of the product. The yield is 42.7%. The yield is the percentage of the weight of the product to the theoretical output calculated based on HO[GGCAU]OE.

The $^{31}$PNMR spectrum and M$^-$ of the product are detected. They are fully consistent with the theoretical values of $^{31}$PNMR spectrum and M$^-$ of the target compound, proving this product indeed has the structure of Formula (3).

(28) Synthesize decamer HO[ACUUCAAAUU]OE (SEQ ID NO:4)

DMTr[ACUUC]PO$^-$ (4.86 g, 1.43 mmol) obtained in Step (24) and HO[AAAUU]OE (3.70 g, 1.19 mmol) obtained in Step (26) are added to a 100 ml round-bottomed flask and dissolved in 10 ml of anhydrous pyridine. MSNT (0.99 g, 3.33 mmol) is added. The reaction lasts 4 h at room temperature. After TLC indicates thorough reaction, 1 ml of saturated NaHCO$_3$ solution is added to terminate the reaction. 100 ml of CH$_2$Cl$_2$ is added. Then it is washed with 50 ml of saturated NaHCO$_3$ solution once and with 50 ml of water once. It is dried with anhydrous Na$_2$SO$_4$. The solvent is removed by rotary evaporation. After separation in a column, 150 ml of 2% TsOH CH$_2$Cl$_2$/CH$_3$OH (v:v=7:3) solution is added to the obtained product and violently stirred at 0° C. for 10 min. The solution is immediately neutralized with a saturated NaHCO$_3$ solution. An organic phase is separated. It is washed with 50 ml of saturated NaHCO$_3$ solution once. After the organic phase is dried with anhydrous Na$_2$SO$_4$, the solvent is removed. After purification by column chromatography (the eluent is CH$_2$Cl$_2$/CH$_3$OH (v:v=10:1)), 4.6 g of the product is obtained. The yield is 63.5%. The yield is the percentage of the weight of the product to the theoretical output calculated based on HO[AAAUU]OE.

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).

(29) Synthesize henicosamer DMTr[CCUUGAGGCAUAC-UUCAAAUU]OE (SEQ ID NO:2):

DMTr[CCUUGAGGCAU]PO$^-$ (SEQ ID NO:3) (2.80 g, 0.39 mmol) obtained in Step (27) and HO[ACUU-CAAAUU]OE (SEQ ID NO:4) (2.17 g, 0.36 mmol) obtained in Step (28) are added to a 50 ml round-bottomed flask and dissolved in 10 ml of anhydrous pyridine. MSNT (321 mg, 1.08 mmol) is added. The reaction lasts 10 h at room temperature. 1 ml of saturated NaHCO$_3$ solution is added to terminate the reaction. 100 ml of CH$_2$Cl$_2$ is added. It is washed with 50 ml of saturated NaHCO$_3$ solution once and with 50 ml of water once. It is dried with anhydrous Na$_2$SO$_4$. The solvent is removed by rotary evaporation. After purification by column chromatography (the eluent is CH$_2$Cl$_2$/CH$_3$OH (v:v=10:1)), 2.48 g of the product is obtained. The yield is 50.1%. The yield is the percentage of the weight of the product to the theoretical output calculated based on HO[ACUUCAAAUU]OE (SEQ ID NO:4).

The $^{31}$PNMR spectrum and M$^-$ of the product are detected. They are fully consistent with the theoretical values of $^{31}$PNMR spectrum and M$^-$ of the target compound, proving this product indeed has the structure of Formula (4).

By now, fully protected henicosamer RNA DMTr[CCUUGAGGCAUACUUCAAAUU]OE (SEQ ID NO:2) is obtained through synthesis by liquid-phase process.

(30) Deprotection:

10 mg of fully protected henicosamer RNA DMTr[CCUUGAGGCAUACUUCAAAUU]OE (SEQ ID NO:2) obtained in Step (29) is dissolved in 0.5 ml of dioxane. 1 ml of 25 mass % aqua ammonia is added. The solution is shaken and mixed evenly and rests at room temperature for 40 h. After the reaction is completed, the solution is concentrated under reduced pressure to remove the solvent till fully dry. The remaining solid is redissolved in 100 μl of dimethyl sulfoxide. 125 μl of TEA.3HF is added. After even mixing, the solution is heated to 65° C. and reacts 2.5 h. 1 ml of normal butanol precooled to −20° C. is added. Oligonucleotide settles. The precipitate is collected by centrifuge, and 3 mg of a crude product is obtained. The product is refined and purified by reverse phase ODS column chromatograph. The concrete operation steps refer to literature (Molecular Cloning: A Laboratory Manual (Edition 3), published by Science Press in September 2002). Then it is frozen and dried to obtain 1.6 mg of the target product.

Mass spectrometry of Shimadzu AXIMA-CFR plus MALDI-TOF is used to analyze the mass of the target product obtained in Step (30), the obtained mass spectrum is represented by FIG. 1.

The result of mass spectrometry indicates: The oligonucleotide obtained in Step (30) has two peaks of which m/z is 6701.97 and 3351.22 respectively. The two peaks are the single-charge peak and double-charge peak of the oligonucleotide and are consistent with theoretic charge peaks (m/z: 6702 and 3351). There aren't other impurity peaks in the mass spectrum. Therefore, the result of mass spectrometry indicates: the oligonucleotide obtained in Step (30) has correct mass and high purity.

Figure 2:
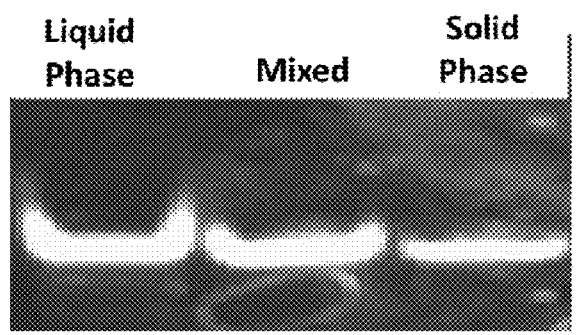
FIG. 2 is a chart for polyacrylamide gel electrophoresis (PAGE) of the deprotected henicosamer RNA CCUUGAG-GCAUACUUCAAAUU (SEQ ID NO:1) obtained in Example 1 and the product with a same sequence obtained by solid-phase synthesis process.

300 ng of the product obtained in Step (30), 300 ng of the product obtained from solid-phase synthesis in ABI3900 RNA solid-phase synthesizer and having the target sequence (5'-CCUUGAGGCAUACUUCAAAUU-3' (SEQ ID NO:1)) (Shanghai GenePharma Co., Ltd.), and 300 ng of a sample made by equally mixing the above two products undergo PAGE detection. The detection result is represented by FIG. 2. The result indicates: The oligonucleotides of a same sequence synthesized by two different processes have the same band position on PAGE. After mixing of the two samples, the band positions are still same without obvious impurity bands. This proves the oligonucleotides of a same target sequence synthesized by two different processes have a same electrophoretic mobility.

By applying small RNA cloning and sequencing techniques (Bartel, D. P., (2004), Cell, Issue 116, page 281) and using a small RNA cloning kit of TaKaRa (product No.: DRR065), the oligonucleotide of the product obtained in Step (30) is cloned. For concrete operation steps, please refer to kit specification. After successful cloning, it is sent to Invitrogen to determine the sequence of bases. The concrete operation steps refer to literature (Roth, M. J et al, (1985), Journal of Biological Chemistry, Issue 260, page 9326).

The cloning and sequencing result is as follows: 5'-CCUUGAGGCAUACUUCAAAUU-3' (SEQ ID NO:1), proving the base sequence of the product obtained in Step (30) is indeed the target sequence.

Example 2

This example synthesizes deprotected oligonucleotide with a target sequence 5'-UUUGAAGUAUGCCU-CAAGGUU-3' (SEQ ID NO:5). This target sequence and the base sequence of the product in Example 1 are partially reversely complementary.

Figure 5:
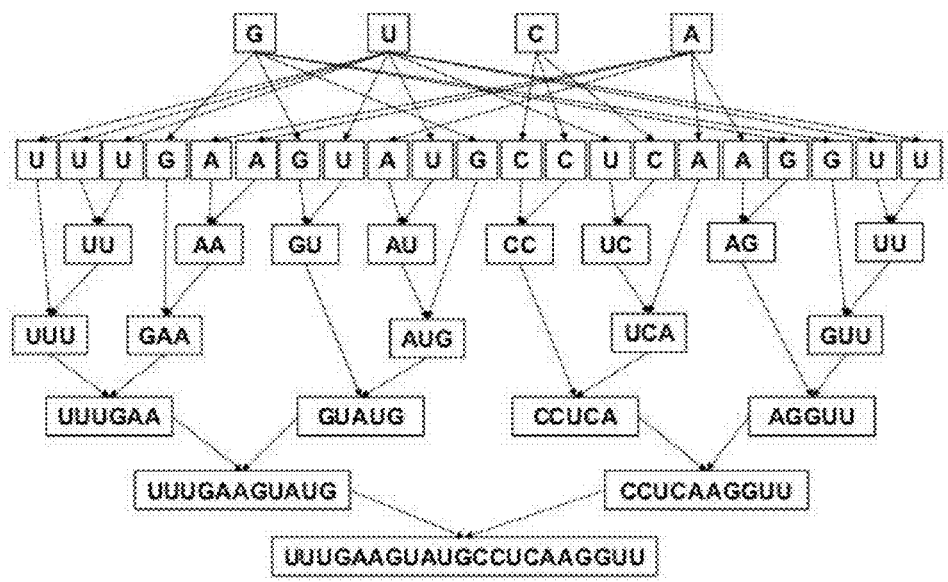
FIG. 5 is a schematic of the synthesis strategy of Example 2.

The synthesis in this example includes 19 steps according to the synthesis strategy represented by FIG. 5.
(1) Synthesize Dimer HO[AA]OE with Formula (2):

It is synthesized by a process same as Step (13) in Example 1 except that HO[A]OE obtained in Step (5) in Example 1 substitutes HO[U]OE obtained in Step (6) in Example 1.

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).
(2) Synthesize Dimer DMTr[GU]PO$^-$:

It is synthesized by a process same as Step (9) and Step (10) in Example 1 except that DMTr[G]PO$^-$ obtained in Step (3) in Example 1 substitutes DMTr[A]PO$^-$ obtained in Step (1) in Example 1, and HO[U]OE obtained in Step (6) in Example 1 substitutes HO[A]OE obtained in Step (5) in Example 1.

The $^{31}$PNMR spectrum and M$^-$ of the product are detected. They are fully consistent with the theoretical values of $^{31}$PNMR spectrum and M$^-$ of the target compound, proving this product indeed has the structure of Formula (3).

(3) Synthesize Dimer DMTr[AU]PO$^-$:

It is synthesized by a process same as Step (9) and Step (10) in Example 1 except that HO[U]OE obtained in Step (6) in Example 1 substitutes HO[A]OE obtained in Step (5) in Example 1.

The $^{31}$PNMR spectrum and M$^-$ of the product are detected. They are fully consistent with the theoretical values of $^{31}$PNMR spectrum and M$^-$ of the target compound, proving this product indeed has the structure of Formula (3).
(4) Synthesize Dimer DMTr[CC]PO$^-$:

It is synthesized by a process same as Step (9) and Step (10) in Example 1 except that DMTr[C]PO$^-$ obtained in Step (4) in Example 1 substitutes DMTr[A]PO$^-$ obtained in Step (1) in Example 1, and HO[C]OE obtained in Step (8) in Example 1 substitutes HO[A]OE obtained in Step (5) in Example 1.

The $^{31}$PNMR spectrum and M$^-$ of the product are detected. They are fully consistent with the theoretical values of $^{31}$PNMR spectrum and M$^-$ of the target compound, proving this product indeed has the structure of Formula (3).
(5) Synthesize Dimer DMTr[UC]PO$^-$:

It is synthesized by a process same as Step (9) and Step (10) in Example 1 except that DMTr[U]PO$^-$ obtained in Step (2) in Example 1 substitutes DMTr[A]PO$^-$ obtained in Step (1) in Example 1, and HO[C]OE obtained in Step (8) in Example 1 substitutes HO[A]OE obtained in Step (5) in Example 1.

The $^{31}$PNMR spectrum and M$^-$ of the product are detected. They are fully consistent with the theoretical values of $^{31}$PNMR spectrum and M$^-$ of the target compound, proving this product indeed has the structure of Formula (3).
(6) Synthesize Dimer DMTr[AG]PO$^-$:

It is synthesized by a process same as Step (9) and Step (10) in Example 1 except that HO[G]OE obtained in Step (7) in Example 1 substitutes HO[A]OE obtained in Step (5) in Example 1.

The $^{31}$PNMR spectrum and M$^-$ of the product are detected. They are fully consistent with the theoretical values of $^{31}$PNMR spectrum and M$^-$ of the target compound, proving this product indeed has the structure of Formula (3).
(7) Synthesize Trimer DMTr[UUU]PO$^-$:

It is synthesized by a process same as Step (18) in Example 1 except that DMTr[U]PO$^-$ obtained in Step (6) in Example 1 substitutes DMTr[C]PO$^-$ obtained in Step (4) in Example 1, and HO[UU]OE obtained in Step (17) in Example 1 substitutes HO[CU]OE obtained in Step (14) in Example 1.

The $^{31}$PNMR spectrum and M$^-$ of the product are detected. They are fully consistent with the theoretical values of $^{31}$PNMR spectrum and M$^-$ of the target compound, proving this product indeed has the structure of Formula (3).
(8) Synthesize Trimer HO[GAA]OE:

It is synthesized by a process same as Step (19) in Example 1 except that DMTr[G]PO$^-$ obtained in Step (3) in Example 1 substitutes DMTr[U]PO$^-$ obtained in Step (2) in Example 1, and HO[AA]OE obtained in Step (1) in Example 1 substitutes HO[GA]OE obtained in Step (15) in Example 1.

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).
(9) Synthesize Trimer HO[AUG]OE:

It is synthesized by a process same as Step (19) in Example 1 except that DMTr[AU]PO$^-$ obtained in Step (3) in Example 2 substitutes DMTr[U]PO$^-$ obtained in Step (2)

in Example 1, and HO[G]OE obtained in Step (7) in Example 1 substitutes HO[GA]OE obtained in Step (15) in Example 1.

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).

(10) Synthesize Trimer HO[UCA]OE:

It is synthesized by a process same as Step (19) in Example 1 except that DMTr[UC]PO$^-$ obtained in Step (5) in Example 2 substitutes DMTr[U]PO$^-$ obtained in Step (5) in Example 1, and HO[A]OE obtained in Step (5) in Example 1 substitutes HO[GA]OE obtained in Step (15) in Example 1.

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).

(11) Synthesize Trimer HO[GUU]OE:

It is synthesized by a process same as Step (19) in Example 1 except that DMTr[G]PO$^-$ obtained in Step (3) in Example 1 substitutes DMTr[U]PO$^-$ obtained in Step (2) in Example 1, and HO[UU]OE obtained in Step (17) in Example 1 substitutes HO[GA]OE obtained in Step (15) in Example 1.

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).

(12) Synthesize Hexamer DMTr[UUUGAA]PO$^-$:

It is synthesized by a process same as Step (23) in Example 1 except that DMTr[UUU]PO$^-$ obtained in Step (7) in Example 2 substitutes DMTr[CCU]PO$^-$ obtained in Step (18) in Example 1, and HO[GAA]OE obtained in Step (8) in Example 2 substitutes HO[UGA]OE obtained in Step (19) in Example 1.

The $^{31}$PNMR spectrum and M$^-$ of the product are detected. They are fully consistent with the theoretical values of $^{31}$PNMR spectrum and M$^-$ of the target compound, proving this product indeed has the structure of Formula (3).

(13) Synthesize Pentamer HO[GUAUG]OE:

It is synthesized by a process same as Step (25) in Example 1 except that DMTr[GU]PO$^-$ obtained in Step (2) in Example 2 substitutes DMTr[GG]PO$^-$ obtained in Step (11) in Example 1, and HO[AUG]OE obtained in Step (9) in Example 1 substitutes HO[CAU]OE obtained in Step (20) in Example 1.

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).

(14) Synthesize Pentamer DMTr[CCUCA]PO$^-$:

It is synthesized by a process same as Step (23) in Example 1 except that DMTr[CC]PO$^-$ obtained in Step (4) in Example 2 substitutes DMTr[CC]PO$^-$ obtained in Step (18) in Example 1, and HO[UCA]OE obtained in Step (10) in Example 2 substitutes HO[UGA]OE obtained in Step (19) in Example 1.

The $^{31}$PNMR spectrum and M$^-$ of the product are detected. They are fully consistent with the theoretical values of $^{31}$PNMR spectrum and M$^-$ of the target compound, proving this product indeed has the structure of Formula (3).

(15) Synthesize Pentamer HO[AGGUU]OE:

It is synthesized by a process same as Step (25) in Example 1 except that DMTr[AG]PO$^-$ obtained in Step (6) in Example 2 substitutes DMTr[GG]PO$^-$ obtained in Step (11) in Example 1, and HO[GUU]OE obtained in Step (11) in Example 2 substitutes HO[CAU]OE obtained in Step (20) in Example 1.

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).

(16) Synthesize undecamer DMTr[UUUGAAGUAUG]PO$^-$ (SEQ ID NO:6):

It is synthesized by a process same as Step (27) in Example 1 except that DMTr[UUUGAA]PO$^-$ obtained in Step (12) in Example 2 substitutes DMTr[CCUUGA]PO$^-$ obtained in Step (23) in Example 1, and HO[GUAUG]OE obtained in Step (13) in Example 2 substitutes HO[GGCAU]OE obtained in Step (25) in Example 1.

The $^{31}$PNMR spectrum and M$^-$ of the product are detected. They are fully consistent with the theoretical values of $^{31}$PNMR spectrum and M$^-$ of the target compound, proving this product indeed has the structure of Formula (3).

(17) Synthesize decamer HO[ACUUCAAAUU]OE (SEQ ID NO:4)

It is synthesized by a process same as Step (28) in Example 1 except that DMTr[CCUCA]PO$^-$ obtained in Step (14) in Example 2 substitutes DMTr[ACUUC]PO$^-$ obtained in Step (24) in Example 1, and HO[AGGUU]OE obtained in Step (15) in Example 2 substitutes HO[AAAUU]OE obtained in Step (26) in Example 1.

The $^{31}$PNMR spectrum and M$^-$ of the product are detected. They are fully consistent with the theoretical values of $^{31}$PNMR spectrum and M$^-$ of the target compound, proving this product indeed has the structure of Formula (2).

(18) Synthesize henicosamer DMTr[UUUGAAGUAUGCCUCAAGGUU]OE (SEQ ID NO:7):

It is synthesized by a process same as Step (29) in Example 1 except that DMTr[UUUGAAGUAUG]PO$^-$ (SEQ ID NO:6) obtained in Step (16) in Example 2 substitutes DMTr[CCUUGAGGCAU]PO$^-$ (SEQ ID NO:3) obtained in Step (27) in Example 1, and HO[ACUUCAAAUU]OE (SEQ ID NO:4) obtained in Step (17) in Example 2 substitutes HO[ACUUCAAAUU]OE (SEQ ID NO:4) obtained in Step (28) in Example 1.

The $^{31}$PNMR spectrum and M$^-$ of the product are detected. They are fully consistent with the theoretical values of $^{31}$PNMR spectrum and M$^-$ of the target compound, proving this product indeed has the structure of Formula (4).

By now, fully protected henicosamer RNA DMTr[UUUGAAGUAUGCCUCAAGGUU]OE (SEQ ID NO:7) is obtained through synthesis by liquid-phase process.

(19) Deprotection

Deprotection is conducted by a process same as Step (30) in Example 1 except that DMTr[UUUGAAGUAUGCCUCAAGGUU]OE (SEQ ID NO:7) obtained in Step (18) in Example 2 substitutes DMTr[CCUUGAGGCAUACUUCAAAUU]OE (SEQ ID NO:2) obtained in Step (29) in Example 1.

Mass spectrometry, electrophoresis result and sequencing result all support that the base sequence of the product in Step (19) is indeed the target sequence.

Example 3

By an RNA interference test, this example detects the bioactivity consistence between the product obtained by the process provided by the present invention for liquid-phase synthesis and the product of a same sequence obtained by solid-phase synthesis process.

The product in Example 1 and the product in Example 2 are equally mixed (5 nmol) and heated to 75° C. The temperature is held for 10 min. Then it is naturally and slowly cooled to room temperature to obtain double-chain siRNA with the following sequence.

The target gene of small interference RNA (siRNA) with a known sequence of CCUUGAGGCAUACUUCAAA (SEQ ID NO:8) is hepatitis B virus X protein (HBV-X). Therefore, theoretically the said double-chain siRNA has the activity inhibiting the expression of HBX gene.

Through quantitative PCR, the inhibitory activities of the product obtained by the process provided by the present invention for liquid-phase synthesis and the product of a same sequence obtained by solid-phase synthesis process to HBV-X gene expression in HepG2.2.15 cells are detected.
(1) Cultivation of HepG2.2.15 Cells A complete medium containing 10% fetal calf serum, 2 mM L-glutamine and 380 μg/ml G418 DMEM is used to inoculate HepG2.2.15 cells (purchased from the People's Hospital of Peking University) on a 24-well culture plate at a density of 1×10⁵ cells/well and cultivated in an incubator with a temperature of 37° C. and a CO₂ concentration of 5%.
(2) Transfection of siRNA Lipofectamine™2000 liposome bought from Invitrogen is used to compare the double-chain siRNA obtained in Example 7, the double-chain siRNA of a same sequence synthesized by solid-phase synthesis process (purchased from Shanghai GenePharma Co., Ltd.), the double-chain siRNA(PC) with a positive effect reported in literature (the sequence is 5'-UCACCAUACUGCACUCAGG-3' (SEQ ID NO:9), WU et al., "RNA Interference inhibits replication and expression of hepatitis B virus in mice" Natl. Med. J. China (Mar. 9, 2005) Vol. 85, No. 9, pp. 630-634) and the irrelevant double-chain siRNA (NC) (all purchased from Shanghai GenePharma Co., Ltd.). They are transfected to the HepG2.2.15 cells in Step (1) of this example according to the transfection amount of 0.06 nmol/well. Meanwhile, sterilized deionized water is used as a blank control of siRNA transfection. For concrete operation steps, please refer to the specification of Lipofectamine™2000 and literature (WU et al., "RNA Interference inhibits replication and expression of hepatitis B virus in mice" Natl. Med. J. China (Mar. 9, 2005) Vol. 85, No. 9, pp. 630-634).
(3) The expression level of mRNA of HBX gene in HepG2.2.15 cells transfected with siRNA in Step (2) of this example is detected by Real Time-PCR process. Glyceraldehyde-3-phosphate dehydrogenase (GAPDH) is set as an internal control gene. The sequences of the used primers are as follows:

| Gene | Upstream primer | Downstream primer |
|------|-----------------|-------------------|
| HBV-X | 5'-actctctcgtcccttct cc-3' (SEQ ID NO: 10) | 5'-ggtcgttgacattgcaga ga-3' (SEQ ID NO: 11) |
| GAPDH | 5'-ctctgctcctcctgttcg ac-3' (SEQ ID NO: 12) | 5'-acgaccaaatccgttgac tc-3' (SEQ ID NO: 13) |

The concrete operation steps refer to literature (Molecular Cloning (Edition 3), published by Science Press in September 2002). The inhibitory activity of siRNA is calculated with the following formula.

Inhibitory activity of siRNA=1−(copy number of HBV gene after siRNA transfection/copy number of GAPDH after siRNA transfection)/(copy number of HBV gene in the blank control/copy number of GAPDH in the blank control).

Figure 3:
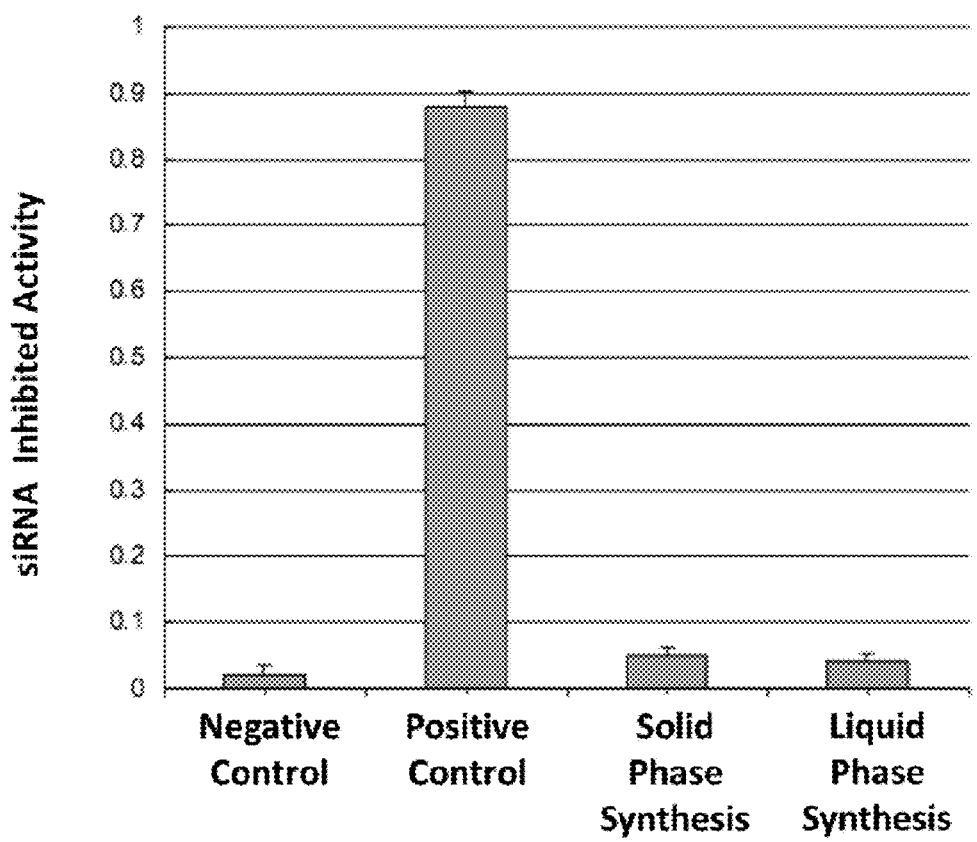
FIG. 3 is a drawing showing the result of RNA interference test in Example 3.

The result of cell siRNA interference test is represented by FIG. 3: The mRNA level of HBV-X gene in negative irrelevant siRNA (NC) control group is not be lowered, while liquid-phase synthesis product siRNA and solid-phase synthesis product siRNA have the same ability as the positive control (PC) in inhibiting HBV-X gene expression. This proves liquid-phase synthesis product siRNA and solid-phase synthesis product siRNA obtained in Example 2 have same bioactivity in inhibiting expression of target genes.

Example 4

This example synthesizes dotetracontamer oligonucleotide DMTr[CCUUGAGGCAUACUUCAAAUUUUUGAAGUAUGCCUCAAGGUU]OE (SEQ ID NO:14).
(1) Synthesize DMTr[CCUUGAGGCAUACUUCAAAUU]PO⁻ (SEQ ID NO:15)

3.18 g (0.24 mmol) of DMTr[CCUUGAGGCAUACUUCAAAUU]OE (SEQ ID NO:16) obtained in Step (29) of Example 1 is dissolved in 10 ml of pyridine/triethylamine/water (v:v:v=3:1:1) and stirred at room temperature for 30 min. After TLC indicates thorough reaction and the solvent is removed by rotary evaporation, the remnant is redissolved in 100 ml of CH₂Cl₂ and washed with 1M TEAB solution three times (50 ml per time). An organic phase is separated and dried with anhydrous Na₂SO₄. After the solvent is removed, 2.64 g of the product is obtained.
(2) Synthesize HO[UUUGAAGUAUGCCUCAAGGUU]OE (SEQ ID NO:17)

2.84 g (0.2 mmol) of DMTr[UUUGAAGUAUGCCUCAAGGUU]OE (SEQ ID NO:18) obtained in Step (18) of Example 2 is added to 25 ml of 2 wt % TsOH CH₂Cl₂/CH₃OH (v:v=7:3) solution and violently stirred at 0° C. for 10 min. It is immediately neutralized with a saturated NaHCO₃ solution. An organic phase is separated. Then it is washed with 25 ml of saturated NaHCO₃ solution once. After the organic phase is dried with anhydrous Na₂SO₄, the solvent is removed. After purification by column chromatography (the used eluent is CH₂Cl₂/CH₃OH (v:v=10:1)), 2.56 g of the product is obtained.
(3) Synthesize Dotetracontamer DMTr[CCUUGAGGCAUACUUCAAAUUUUUGAAGUAUGCCUCAAGGUU]OE (SEQ ID NO:14):

It is synthesized by a process same as Step (29) in Example 1 except that DMTr[CCUUGAGGCAUACUUCAAAUU]PO⁻ (SEQ ID NO:15) obtained in Step (1) in Example 4 substitutes DMTr[CCUUGAGGCAU]PO⁻ (SEQ ID NO:3) obtained in Step (27) in Example 1, and HO[UUUGAAGUAUGCCUCAAGGUU]OE (SEQ ID NO:17) obtained in Step (2) in Example 4 substitutes HO[ACUUCAAAUU]OE (SEQ ID NO:4) obtained in Step (28) in Example 1. 1.21 g of the product is obtained. The yield is 30.1%. The yield is the percentage of the weight of the product to the theoretical output calculated based on HO[UUUGAAGUAUGCCUCAAGGUU]OE (SEQ ID NO:17).

The ³¹PNMR spectrum and M⁻ of the product are detected. They are fully consistent with the theoretical values of ³¹PNMR spectrum and M⁻ of the target product, proving this product indeed has the structure of Formula (4).

By now, fully protected dotetracontamer RNA DMTr[CCUUGAGGCAUACUUCAAAUUUUUGAAGUAUGCCUCAAGGUU]OE (SEQ ID NO:14) is obtained by liquid-phase synthesis.

What is claimed is:

1. A protected nucleotide or oligonucleotide represented by Formula (1):

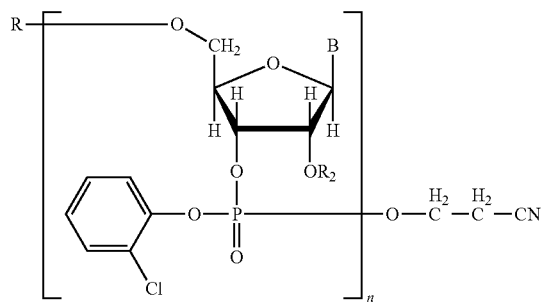

Formula (1)

wherein, R is 4,4'-dimethoxytrityl; n is an integer in the range of 1-100;

B is a 9-guaninyl group with its exocyclic amino group protected by an acyl substituent, an 9-adeninyl group with its exocyclic amino group protected by an acyl substituent, a 1-cytosinyl group with its exocyclic amino group protected by an acyl substituent, a 1-thyminyl group or 1-uracilyl group, and B of each repeat unit is identical or different; and $R_2$ is tert-butyl dimethyl silyl, phenyl dimethyl silyl, tert-butyl diphenyl silyl or triisopropyl silyl.

2. The protected nucleotide or oligonucleotide according to claim 1, wherein the acyl substituent is benzoyl, isobutyryl or acetyl.

3. A process for a liquid-phase synthesis of a protected oligonucleotide, comprising contacting a compound of Formula (2) with a compound of Formula (3) in a first liquid reaction medium comprising a condensing agent to obtain the compound of Formula (4);

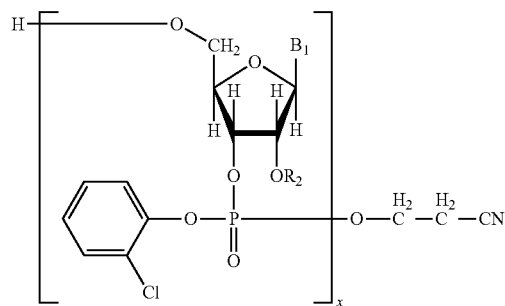

Formula (2)

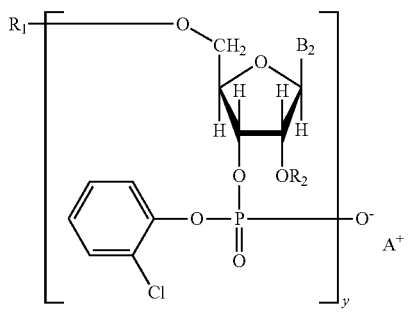

Formula (3)

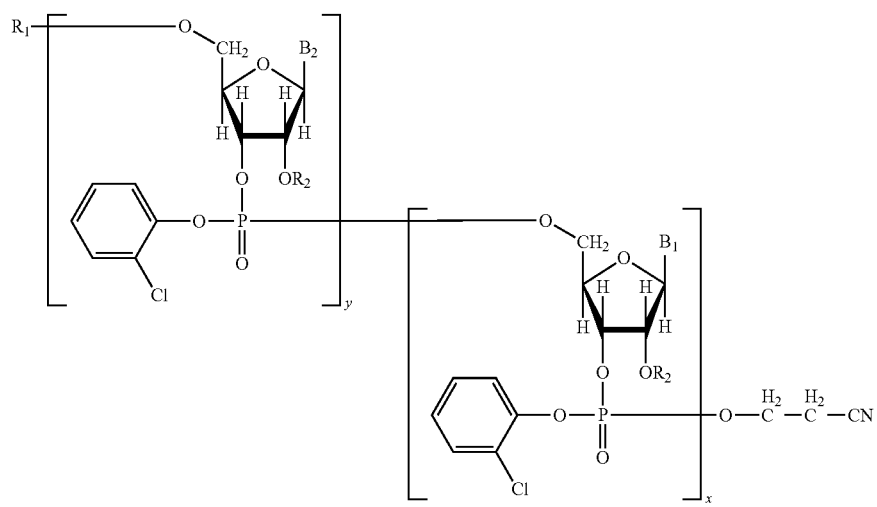

Formula (4)

wherein, $R_1$ is 4,4'-dimethoxytrityl; x is an integer in the range of 1-50; y is an integer in the range of 1-50;

$B_1$ and $B_2$, which are identical or different, are a 9-guaninyl group with its exocyclic amino group protected by an acyl substituent, an 9-adeninyl group with its exocyclic amino group protected by an acyl substituent, a 1-cytosinyl group with its exocyclic amino group protected by an acyl substituent, a 1-thyminyl group or 1-uracilyl group, wherein the acyl substituent is benzoyl, isobutyryl or acetyl, and $B_1$ and $B_2$ of each repeat unit are identical or different;

$R_2$ is tert-butyl dimethyl silyl, phenyl dimethyl silyl, tert-butyl diphenyl silyl or triisopropyl silyl; and $A^+$ is trialkylammonium ion or dialkylammonium ion.

4. The process according to claim 3, wherein the alkyl groups in the trialkylammonium ion or dialkylammonium ion are identical or different and each has 1-6 carbon atoms.

5. The process according to claim 3, wherein in the contacting step: the condensing agent is 1-mesitylene-sulfonyl-triazole, 1-mesitylene-sulfonyl-(3-nitro)-triazole, 1-mesitylene-sulfonyl-tetrazole, 1-triisopropyl-phenyl-sulfonyl-triazole, 1-triisopropyl-phenyl-sulfonyl-(3-nitro)-triazol, 1-triisopropyl-phenyl-sulfonyl-tetrazole, or combinations thereof; the first liquid reaction medium further comprises pyridine, dichloromethane, acetonitrile, dioxane, tetrahydrofuran, or combinations thereof; relative to 1 mol of the compound of Formula (3), the amount of the condensing agent is 2-20 mol, the volume of the first liquid reaction medium is 2-50 L, and when x is greater than or equal to 1, the amount of the compound of Formula (2) is 0.3-1.25 mol; the reaction temperature is 0-50° C.; and the reaction time is 0.5-100 h.

6. The process according to claim 3, further comprising contacting, under conditions of hydrolysis, the compound of Formula (4) with a second liquid reaction medium comprising (a) water and (b) trialkylamine or dialkylamine, to obtain the compound of Formula (5) wherein, $R_1$ is 4,4'-dimethoxytrityl;
x is an integer in the range of 1-50;
y is an integer in the range of 1-50;
$B_1$ and $B_2$, which are identical or different, are a 9-guaninyl group with its exocyclic amino group protected by acyl substituent, an 9-adeninyl group with its exocyclic amino group protected by an acyl substituent, a 1-cytosinyl group with its exocyclic amino group protected by an acyl substituent, a 1-thyminyl group, or 1-uracilyl group, wherein the acyl substituent is benzoyl, isobutyryl, or acetyl, and $B_1$ and $B_2$ of each repeat unit are identical or different; and $R_2$ is tert-butyl dimethyl silyl, phenyl dimethyl silyl, tert-butyl diphenyl silyl, or triisopropyl silyl.

7. The process according to claim 6, wherein relative to 1 mol of the compound of Formula (4), the amount of trialkylamine or dialkylamine is 1-200 mol; the volume of the second liquid reaction medium is 5-50 L; the volume of water is 2-20 L; the reaction temperature is 0-50° C.; and the reaction time is 0.25-2 h.

8. The process according to claim 7, wherein the second liquid reaction medium further comprises pyridine and/or acetonitrile; and the alkyl groups in the trialkylamine or dialkylamine are identical or different, and each has 1-6 carbon atoms.

9. The process according to claim 6, further comprising contacting another compound of Formula (2) with the compound of Formula (5) to obtain the compound of Formula (4).

10. The process according to claim 3, further comprising contacting the compound of Formula (4) with a third reaction medium comprising an organic acid to obtain a compound of Formula (6)

Formula (6)

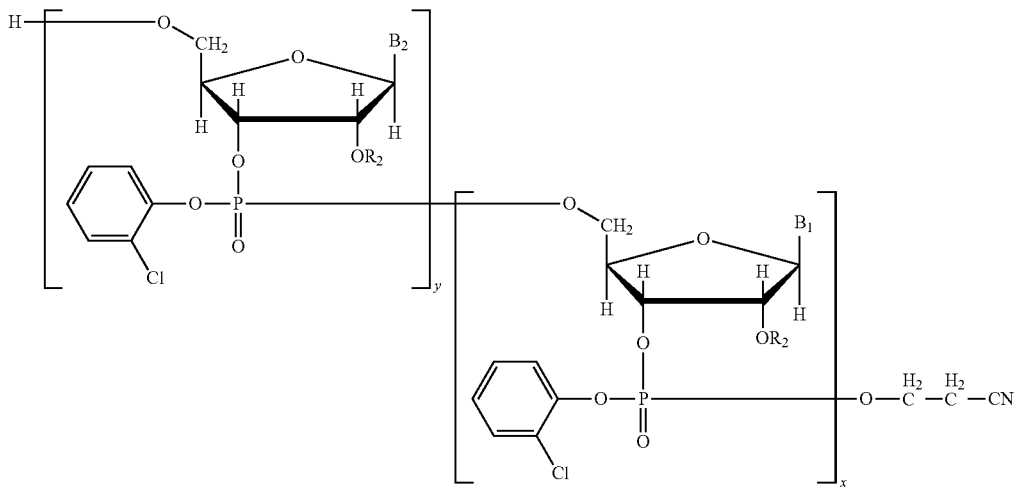

wherein, x is an integer in the range of 1-50;
y is an integer in the range of 1-50;
$B_1$ and $B_2$, which are identical or different, are a 9-guaninyl group with its exocyclic amino group protected by an acyl substituent, an 9-adeninyl group with its exocyclic amino group protected by an acyl substituent, a 1-cytosinyl group with its exocyclic amino group protected by an acyl substituent, a 1-thyminyl group, or 1-uracilyl group, wherein the acyl substituent is benzoyl, isobutyryl, or acetyl, and $B_1$ and $B_2$ of each repeat unit are identical or different; and $R_2$ is tert-butyl dimethyl silyl, phenyl dimethyl silyl, tert-butyl diphenyl silyl, or triisopropyl silyl.

11. The process according to claim 10, wherein in the step of contacting the compound of Formula (4): relative to 1 mol of the compound of Formula (4), the amount of the organic acid is 2-20 mol; the volume of the third liquid reaction medium is 10-150 L; the reaction temperature is −10° C. to 40° C.; the reaction time is 1-60 min; the organic acid is methyl benzenesulfonic acid, benzenesulfonic acid, trichloroacetic acid, dichloroacetic acid, trifluoroacetic acid, or combinations thereof; and the third liquid reaction medium further comprises dichloromethane, trichloromethane, acetonitrile, methanol, or combinations thereof.

12. The process according to claim 10, further comprising contacting another compound of Formula (3) with the compound of Formula (6) to obtain a compound of Formula (4).

13. The process according to claim 3, further comprising contacting the compound of Formula (4) with a fourth liquid reaction medium comprising aqueous ammonia at a concentration of 25-28 mass %, to obtain a compound of Formula (7)

$R_2$ is tert-butyl dimethyl silyl, phenyl dimethyl silyl, tert-butyl diphenyl silyl, or triisopropyl silyl.

14. The process according to claim 13, wherein in the step of contacting the compound of Formula (4): the fourth liquid reaction medium comprises dioxane, acetonitrile, pyridine, ethanol, methanol, or combinations thereof; relative to 1 g of the compound of Formula (4), the volume of aqueous ammonia is 0.02-0.5 L; the volume of the fourth liquid reaction medium is 0.01-0.2 L; the reaction temperature is 10-60° C.; and the reaction time is 5-100 h.

15. A process to obtain the compound of Formula (8) comprising applying the process according to claim 3 to obtain the compound of Formula (4), Formula (7)

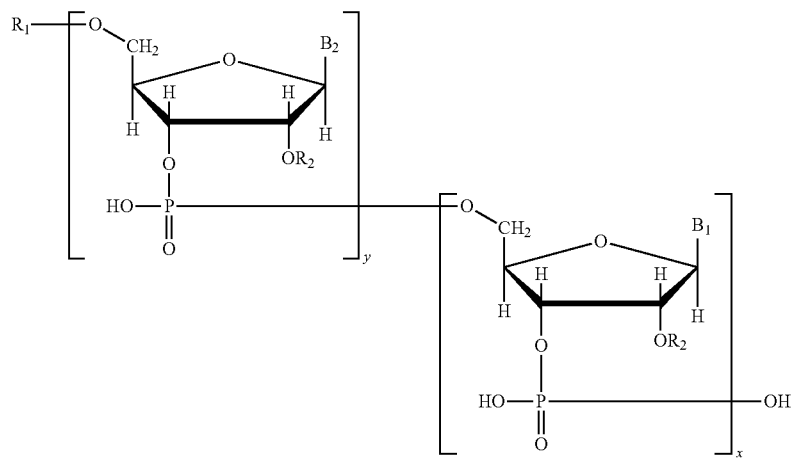

wherein, $R_1$ is 4,4'-dimethoxytrityl;

x is an integer in the range of 1-50;

y is an integer in the range of 1-50;

$B_1$ and $B_2$, which are identical or different, are a 9-guaninyl group, an 9-adeninyl group, a 1-cytosinyl group, a 1-thyminyl group, or 1-uracilyl group, and $B_1$ and $B_2$ of each repeat unit are identical or different; and contacting the compound of Formula (4) with a fourth liquid reaction medium comprising aqueous ammonia at a concentration of 25-28 mass %, to obtain Formula (7) of claim 14, and contacting the compound of Formula (7) with a fifth liquid reaction medium comprising triethylamine trihydrofluoric acid (TEA.3HF) to obtain the compound of Formula (8), Formula (8)

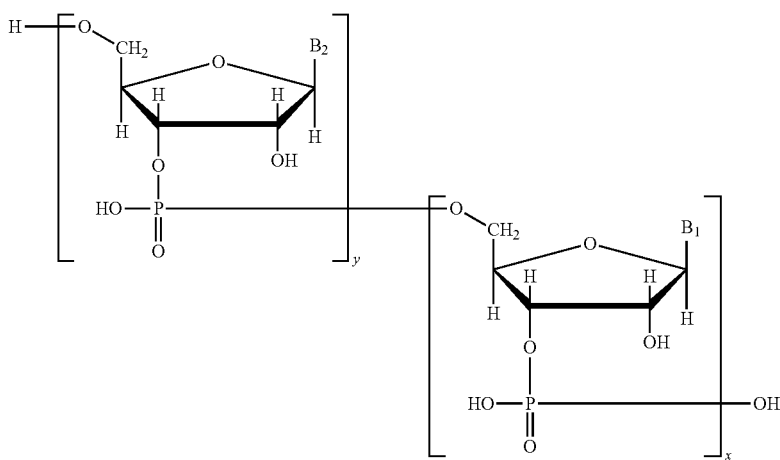

wherein, x is an integer in the range of 1-50;
y is an integer in the range of 1-50; and
$B_1$ and $B_2$, which are identical or different, are a 9-guaninyl group, an 9-adeninyl group, a 1-cytosinyl group, a 1-thyminyl group, or 1-uracilyl group, and $B_1$ and $B_2$ of each repeat unit are identical or different.

16. The process according to claim 15, wherein in the step of contacting the compound of Formula (7): the fifth liquid reaction medium is comprises dimethyl sulfoxide; relative to 1 g of the compound of Formula (7), the volume of TEA.3HF is 0.002-0.05 L; the volume of the fifth liquid reaction medium is 0.002-0.05 L; the reaction temperature is 40-85° C.; and the reaction time is 1-5 h.

17. The process according to claim 3, wherein x is an integer in the range of 10-50, y is an integer in the range of 10-50, or both.

18. The process according to claim 3, wherein x is an integer in the range of 15-50, y is an integer in the range of 15-50, or both.

19. The process according to claim 3, wherein x is an integer in the range of 21-50, y is an integer in the range of 21-50, or both.

\* \* \* \* \*